US012006365B2

(12) United States Patent
Smith et al.

(10) Patent No.: US 12,006,365 B2
(45) Date of Patent: *Jun. 11, 2024

(54) HUMAN ANTI-SEMAPHORIN 4D ANTIBODY

(71) Applicant: VACCINEX, INC., Rochester, NY (US)

(72) Inventors: Ernest S. Smith, W. Henrietta, NY (US); Angelica Cornelison, Pittsford, NY (US); Maria Scrivens, Rochester, NY (US); Mark Paris, Mendon, NY (US); Maurice Zauderer, Pittsford, NY (US)

(73) Assignee: VACCINEX, INC., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/813,375

(22) Filed: Jul. 19, 2022

(65) Prior Publication Data
US 2022/0356249 A1    Nov. 10, 2022

Related U.S. Application Data

(63) Continuation of application No. 16/611,209, filed as application No. PCT/US2018/031263 on May 4, 2018, now Pat. No. 11,427,634.

(60) Provisional application No. 62/501,981, filed on May 5, 2017.

(51) Int. Cl.
A61K 39/395    (2006.01)
A61K 39/00     (2006.01)
C07K 16/00     (2006.01)
C07K 16/28     (2006.01)
C07K 16/46     (2006.01)

(52) U.S. Cl.
CPC .... C07K 16/2803 (2013.01); A61K 2039/505 (2013.01); C07K 2317/33 (2013.01); C07K 2317/73 (2013.01); C07K 2317/76 (2013.01); C07K 2317/92 (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis | |
| 4,741,900 A | 5/1988 | Alvarez | |
| 4,873,192 A | 10/1989 | Kunkel | |
| 5,116,964 A | 5/1992 | Capon | |
| 5,122,464 A | 6/1992 | Wilson | |
| 5,225,538 A | 7/1993 | Capon | |
| 5,314,995 A | 5/1994 | Fell, Jr. | |
| 5,585,089 A | 12/1996 | Queen | |
| 5,693,761 A | 12/1997 | Queen | |
| 5,693,762 A | 12/1997 | Queen | |
| 5,892,019 A | 4/1999 | Schlom | |
| 5,939,598 A | 8/1999 | Kucherlapati | |
| 6,180,370 B1 | 1/2001 | Queen | |
| 6,737,056 B1 | 5/2004 | Presta | |
| 8,496,938 B2 | 7/2013 | Smith | |
| 9,447,191 B2 | 9/2016 | Takayanagi | |
| 11,427,634 B2* | 8/2022 | Smith | A61P 25/00 |
| 11,597,765 B2* | 3/2023 | Mao | A61P 25/00 |
| 2002/0102208 A1 | 8/2002 | Chinn | |
| 2002/0123057 A1 | 9/2002 | Zauderer | |
| 2004/0132101 A1 | 7/2004 | Lazar | |
| 2009/0081126 A1 | 3/2009 | Smith | |
| 2010/0158902 A1 | 6/2010 | Pogue | |
| 2010/0196385 A1 | 8/2010 | Bedian | |
| 2013/0288927 A1 | 10/2013 | Smith | |
| 2014/0072578 A1 | 3/2014 | Smith | |
| 2014/0099334 A1 | 4/2014 | Fisher | |

FOREIGN PATENT DOCUMENTS

| | | |
|---|---|---|
| CN | 104127862 A | 11/2014 |
| EP | 75444 A2 | 3/1983 |
| EP | 396387 A2 | 11/1990 |
| WO | 8605807 A1 | 10/1986 |
| WO | 8901036 A1 | 2/1989 |
| WO | 8912624 A2 | 12/1989 |
| WO | 9114438 A1 | 10/1991 |
| WO | 9208495 A1 | 5/1992 |
| WO | 9314125 A1 | 7/1993 |
| WO | 02096948 A2 | 12/2002 |
| WO | 2004067034 A1 | 8/2004 |
| WO | 2008100995 A1 | 8/2008 |
| WO | 2010129917 A2 | 11/2010 |
| WO | 2013055922 A1 | 4/2013 |
| WO | 2013148854 A1 | 10/2013 |
| WO | 2013170221 A1 | 11/2013 |
| WO | 2014209802 A1 | 12/2014 |
| WO | 2015054628 A1 | 4/2015 |

(Continued)

OTHER PUBLICATIONS

Abbas et al. (2005) Cellular and Molecular Immunology (5th ed.; Elsevier Health Sciences Division).

Altschul et al., "Gapped BLAST and PSI-BLAST: a new generation of protein database search programs." Nucleic Acids Res. Sep. 1, 1997; 25(17): 3389-3402. Abstract.

Basile et al., "Plexin-B1 Utilizes RhoA and Rho Kinase to Promote the Integrin-dependent Activation of Akt and ERK and Endothelial Cell Motility" Journal of Biological Chemical vol. 282, No. 48, pp. 34888-34895, Nov. 30, 2007.

Bebbington and Hentschel (1987) "The Use of Vectors Based on Gene Amplification for the Expression of Cloned Genes in Mammalian Cells in DNA Cloning" (Academic Press, NY) vol. 3.

(Continued)

Primary Examiner — Maher M Haddad
(74) Attorney, Agent, or Firm — KDW Firm PLLC

(57) ABSTRACT

Compositions and method are provided for treating diseases associated with semaphorin-4D (SEMA4D) pathology, including autoimmune diseases, inflammatory diseases, cancers, neuroinflammatory disorders and neurodegenerative diseases.

27 Claims, 8 Drawing Sheets

Specification includes a Sequence Listing.

(56) References Cited

FOREIGN PATENT DOCUMENTS

| WO | 2015061330 A1 | 4/2015 |
|---|---|---|
| WO | 2016096896 A1 | 6/2016 |

OTHER PUBLICATIONS

Bowers et al. "Decreased Mutation Frequencies among Immunoglobulin G Variable Region Genes during Viremic HIV-1 infection", PLOS One. Jan. 7, 2014; vol. 9, No. 1; pp. 1-15; Genbank Supplement pp. 1-2.
Brochet et al., "IMGT/V-QUEST: the highly customized and integrated system for IG and TR standardized V-J and V-D-J sequence analysis", Nucl Acids Res 36:W503-508 (2008).
Brummell, D.A., et al., "Probing the combining site of an anti-carbohydrate antibody by saturation-mutagenesis: Role of the heavy-chain CDR3 residues", Biochem. 32(4):1180-1187 (1993) Abstract.
Burks, E.A., et al., "In vitro scanning saturation mutagenesis of an antibody binding pocket", Proc. Natl. Acad Sci. USA 94:412-417 (1997).
Campos et al., "Ki-67 and CD100 immunohistochemical expression is associated with local recurrence and poor prognosis in soil tissue sarcomas, respectively", Oncology Letters 5:1527-35 (2013).
Chapman, "PEGylated antigodies and antibody fragments for improved therapy: a review," Adv. in Drug Deliv. Rev. 54:531 (2002).
Ch'ng et al., "Prognostic Significance of CD100 Expression in Soft Tissue Sarcoma" 2007, American Cancer Society, 9 pages.
Chothia and Lesk, "Canonical Structures for the Hypervariable Regions of Immunoglobulins", J. Mol. Biol., 196:901-917 (1987).
Cockett et al., "High level expression of tissue inhibitor of metalloproteinases in Chinese hamster ovary cells using glutamine synthetase gene amplification", Biotechnology 8(7):662-7 (1990).
Conrotto et al., "Sema4D induces angiogenesis through Met recruitment by Plexin B1" Blood Journal, Jun. 1, 2005, vol. 105, No. 11, 9 pages.
Crouse et al., "Expression and amplification of engineered mouse dihydrofolate reductase minigenes" Mar. 1983 Molecular and Cellular Biology 3(2):257-66.
Darwish, Ibrahim A., "Immunoassay Methods and their Applications in Pharmaceutical Analysis: Basic Methodology and Recent Advances" Int J Biomed Sci. Sep. 2006; 2(3): 217-235.
Dayhoff et al., "A Model of Evolutionary Change in Proteins", Atlas of Protein Sequence and Structure (Natl. Biomed. Res. Found., Washington, D.C.), pp. 345-352 (1978).
Delaire et al., "Biological Activity of Soluble CD100. Soluble CD100, Similarly to H-SemaIII, Inhibits Immune Cell Migration" J. Immunol. 166:4348-4354 (2001).
Elhabazi et al., "Biological Activity of Soluble CD100. I. The Extracellular Region of CD100 Is Released from the Surface of T Lymphocytes by Regulated Proteolysis1", J. Immunol. 166:4341-4347 (2001).
Evans et al., "Antibody Blockage of Semaphorin 4D Promotes Immune Infiltration into Tumor and Enhances Response to Other Immunomodulatory Therapies" Cancer Immunology Research 3(6):689-701 (2015).
Felson et al., "American College of Rheumatology. Preliminary definition of improvement in rheumatoid arthritis" Arthritis Rheum. Jun. 1995;38(6):727-35.
Fisher et al., "Generation and preclinical characterization of an antibody specific for SEMA4D", MABS 8(1): 150-162 (2016).
Foecking et al., "Powerful and versatile enhancer-promoter unit for mammalian expression vectors" Gene, 45 (1986) 101-105.
Gentz et al., "Bioassay for trans-activation using purified human immunodeficiency virus tat-encoded protein: trans-activation requires mRNA synthesis" Proc Natl Acad Sci USA. Feb. 1989;86(3):821-4.
Giraudon et al., "Semaphorin CD100 from Activated T Lymphocytes Induces Process Extension Collapse in Oligodendrocytes and Death of Immature Neural Cells", J. Immunol. 172:1246-1255 (2004).
Giraudon et al., "T-cells in neuronal injury and repair", NeuroMolecular Med. 7:207-216 (2005) Abstract.
Ishida et al., "Involvement of CD100, a lymphocyte semaphorin, in the activation of the human immune system via CD72: implications for the regulation of immune and inflammatory responses", Inter. Immunol. 15(8):1027-1034 (2003).
Jalkanen, et al., "Cell Surface Proteoglycan of Mouse Mammary Epithelial Cells is Shed by Cleavage of Its Matrix-binding Ectodomain from Its Membrane-associated Domain" J. Cell. Biol. 105:3087-3096 (1987).
Jalkanen, et al., "Heparan Sulfate Proteoglycans from Mouse Mammary Epithelial Cells: Localization on the Cell Surface with a Monoclonal Antibody" The Journal of Cell Biology. vol. 101, 1985, pp. 976-984.
Kato, Shingo et al. "Semaphorin 4D, a lymphocyte semaphorin, enhances tumor cell motility through binding its receptor, plexinB1, in pancreatic cancer." Cancer science vol. 102, 11 (2011): 2029-37.
Kobayashi et al., "Tryptophan H33 plays an important role in pyrimidine (6-4) pyrimidone photoproduct binding by a high-affinity antibody", Protein Eng. 12(10):879-884 (1999).
Kruger et al., "Semaphorins command cells to move", Nature Rev. Mol. Cell Biol. 6:789-800 (2005) Abstract.
Kumanogoh et al., "Immune semaphorins: a new area of semaphorin research", J Cell Science 116(7):3463-3470 (2003).
Kumanogoh A et al., "Identification of CD72 as a Lymphocyte Receptor for the Class IV Semaphorin CD100: A Novel Mechanism for Regulating B Cell Signaling", Immunity 13:621-631 (2000).
Kumanogoh et al., "Requirement for the Lymphocyte Semaphorin, CD100, in the Induction of Antigen-Specific T Cells and the Maturation of Dendritic Cells 1", J Immunol 169:1175-1181 (2002).
Kumanogoh, A., and Kikutani, H., "CD100-CD72 interaction: a novel mechanism of immune regulation", Trends in Immunol. 22(12):670-676 (2001) Abstract.
Kunkel et al., "Rapid and Efficient Site-Specific Mutagenesis without Phenotypic Selction", Methods Enzymol. 154:367-382 (1987).
Kunkel, T.A., "Rapid and efficient site-specific mutagenesis without phenotypic selection", Proc. Natl. Acad. Sci. USA 82:488-492 (1985).
Leonard et al., "Nonclinical Safety Evaluation of VX15/2503, a Humanized IgG4 Anti-SEMA4D Antibody," Molecular Cancer Therapeutics 14(4):964-972 (2015).
Leong et al., "Adapting pharmacokinetic properties of a humanized anti-interleukin-8 antibody for therapeutic applications using site-specific pegylation" Cytokine. Nov. 7, 2001;16(3):106-19.
Mabry, R., and Snavely, M., "Therapeutic bispecific antibodies: The selection of stable single-chain fragments to overcome engineering obstacles", IDrugs. 13(8):543-9 (2010) Abstract.
Needleman et al., "A general method applicable to the search for similarities in the amino acid sequence of two proteins" Journal of Molecular Biology, vol. 48, Issue 3, Mar. 28, 1970, pp. 443-453.
Okuno, T., et al., "Roles of Sema4D-Plexin-B1 Interactions in the Central Nervous System for Pathogenesis of Experimental Autoimmune Encephalomyelitis", J. Immunol. 184:1499-1506 (2010).
Paradis et al., "An RNAi-Based Approach Identifies Molecules Requred for Glutamatergic and GABAergic Synapse Development", Neuron 53:217-232 (2007).
Pasterkamp, R.J., "R-Ras fills another GAP in semaphorin signalling", TRENDS in Cell Biology 15(2):61-64 (2005).
Patnaik et al., "Safety, Pharmacokinetics, and Pharmacodynamics of a Humanized Anti-Semaphorin 4D Antibody, in a First-In-Human Study of Patients with Advanced Solid Tumors", Clin Cancer Res 22(4):827-836 (2016).
Pearson & Lipman., "Improved Tools for Biological Sequence Comparison" Proceedings of the National Academy of Sciences of the United States of America, 1988, 6 pages.
Seifter et al., "Analysis for protein modifications and nonprotein cofactors" Methods in Enzymolog. vol. 182, 1990, pp. 626-646.
Shi et al., "The Class IV Semaphorin CD100 Plays Nonredundant Roles in the Immune System: Defective Band T Cell Activation in CD100-Deficient Mice", Immunity 13:633-642 (2000).
Sierra et al., "Tumor angiogenesis and progression are enhanced by Sema4D produced by tumor-associated macrophages" Exp Med (2008) 205 (7):1673-1685.

(56) References Cited

OTHER PUBLICATIONS

Chothia, Cyrus., "Domain Association in Immunoglobulin Molecules—The Packing of Variable Domains" J. Mol. Biol. (1985) 186, 651-663.
Riechmann et al., "Reshaping human antibodies for therapy" Nature Nol. 332, Mar. 24, 1988.
Smith, Ernest S et al. "SEMA4D compromises blood-brain barrier, activates microglia, and inhibits remyelination in neurodegenerative disease." Neurobiology of disease vol. 73 (2015): 254-68.
Smith and Waterman, "Comparison of Biosequences", Adv. Appl. Math. 2:482-489 (1981).
Southwell A.L., et al., "Anti-semaphorin 4D immunotherapy ameliorates neuropathology and some cognitive impariement in the YAC128 mouse model of Huntington disease", Neurobiol. Dis. 76:46-56 (2015).
Stamatopoulos, K., et al., "Immunoglobulin Light Chain Repertoire in Chronic Lymphocytic Leukemia", Blood. Nov. 15, 2005; vol. 106, No. 10; pp. 3575-3583; Genbank Supplement pp. 1-2.
Strohlein and Heiss, "The trifunctional antibody catumaxomab in treatment of malignant ascites and peritoneal carcinomatosis", Future Oncol. 6(9):1387-94 (2010) Abstract.
Suzuki et al., "Semaphorins and their receptors in immune cell interactions", Nature Immunology, 2008 Nature Publishing, 7 pages.
Swiercz et al., "Plexin-B1 Directly Interacts with PDZ-RhoGEF/LARG to Regulate RhoA and Growth Cone Morphology", Neuron 35:51-63 (2002).
Tamagnone et al., "Plexins are a Large Family of Receptors for Transmembrane, Secreted, and GPI-Anchored Semaphorins in Vertebrates", Cell 99:71-80 (1999).
Van Gestel et al., "Development and validation of the European League Against Rheumatism response criteria for rheumatoid arthritis. Comparison with the preliminary American College of Rheumatology and the World Health Organization/International League Against Rheumatism Criteria" Arthritis Rheum. Jan. 1996;39(1):34-40.
Voller et al., "Enzyme immunoassays with special reference to ELISA techniques" J Clin Pathol. Jun. 1978; 31(6):507-520.

Wang et al., "Functional soluble CD100/Sema4D released from activated lymphocytes: possible role in normal and pathologic immune responses", Blood 97(11):3498-3504 (2001).
Watanabe et al., "Enhanced Immune Responses in Transgenic Mice Expressing a Truncated Form of the Lymphocyte Semaphorin CD100 1", J Immunol 167:4321-4328 (2001).
Weir et al., "Formatting antibody fragments to mediate specific therapeutic functions" Biochem Soc Trans. Aug. 2002;30(4):512-6.
Wilson et al., "The structure of an antigenic determinant in a protein" vol. 37, Issue 3, Jul. 1984, pp. 767-778.
Witherden, D.A., et al., "The CD100 Receptor Interacts with Its Plexin B2 Ligand to Regulate Epidermal γδ T Cell Function", Immunity 37:314-25 (2012).
Brown et al. Tolerance of single, but not multiple, amino acid replacements in antibody VH CDR 2: a means of minimizing B cell wastage from somatic hypermutation? J. Immuno. May 1996, 3285-91. (Year: 1996).
Vajdos et al. Comprehensive functional maps of the antigen-binding site of an anti-ErbB2 antibody obtained with shotgun scanning mutagenesis. J. Mol. Biol. 2002, Jul 5, 320(2):415-28. (Year: 2002).
Okuno et al., "Roles of Sema4D-plexin-B1 interactions in the central nervous system for pathogenesis of experimental autoimmune encephalomyelitis", J Immunol. 184(3):1499-506 (2010).
Lutz Riechmannt et al., "Reshaping human antibodies for therapy," NATURE vol. 332.24, Mar. 1988, pp. 323-327.
Cyrus Chothia et al., "Domain Association in Immunoglobulin Molecules: The Packing of Variable Domains," J. Mol. Biol., Dec. 1985, Academic Press Inc. 186, 651-663.
Cockett et al., "High level expression of tissue inhibitor of metalloproteinases in Chinese hamster ovary cells using glutamine synthetase gene amplification", Biotechnology 8(7):662-7 (1990). doi: 10.1038/nbt0790-662.
Okuno et al., "Roles of Sema4D-plexin-B1 interactions in the central nervous system for pathogenesis of experimental autoimmune encephalomyelitis", J Immunol. 184(3):1499-506 (2010). doi: 10.4049/jimmunol.0903302.

* cited by examiner

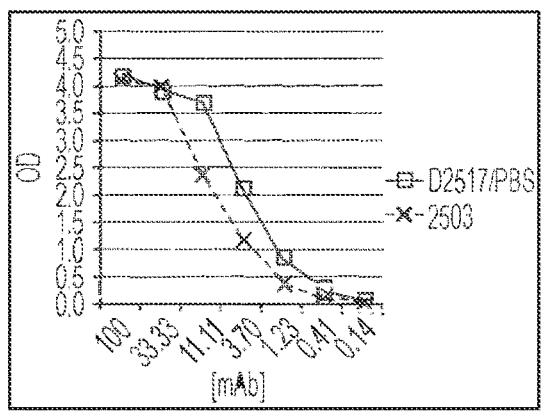
FIG. 1A mAb binding to huCD100-his
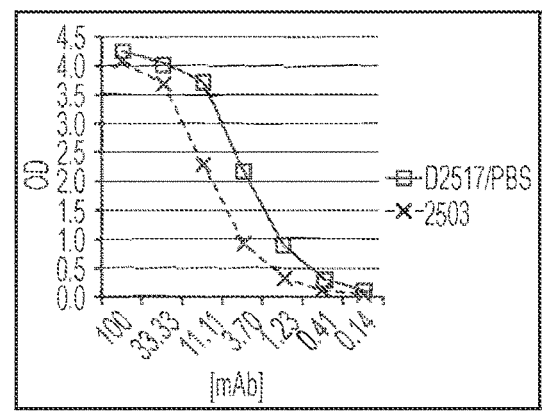
FIG. 1C mAb binding to cynoCD100-his
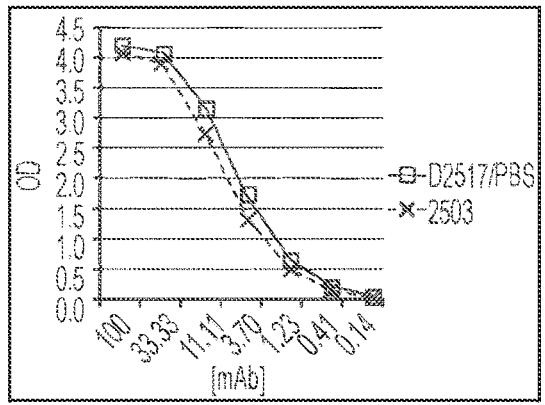
FIG. 1B mAb binding to marmCD100-his
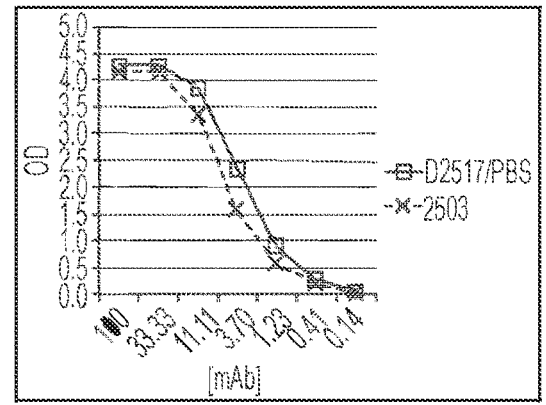
FIG. 1D mAb binding to mouseCD100

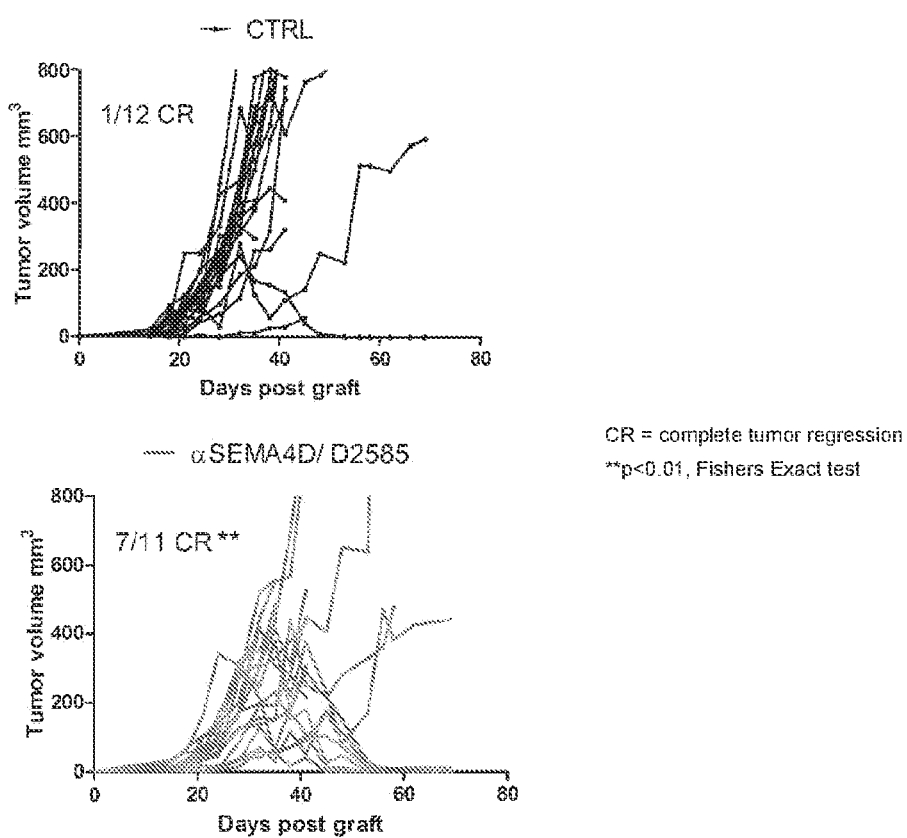

SEQUENCE LISTING

```
Sequence total quantity: 8
SEQ ID NO: 1            moltype = AA  length = 113
FEATURE                 Location/Qualifiers
REGION                  1..113
                        note = Description of Artificial Sequence:
                        Syntheticpolypeptide
source                  1..113
                        mol_type = protein
                        organism = synthetic construct
SEQUENCE: 1
EVQLVESGGG LVQPGGSLRL SCAASGFIFS DYWMVWVRQA PGKGLEYVAH MNQDGGARYY    60
AESVRGRFTI SRDNAKNSLY LQMNSLRAED TAVYYCARDP WGYDSWGQGT LVT          113

SEQ ID NO: 2            moltype = AA  length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 2
DYWMV                                                                5

SEQ ID NO: 3            moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 3
HMNQDGGARY Y                                                         11

SEQ ID NO: 4            moltype = AA  length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 4
DPWGY                                                                5

SEQ ID NO: 5            moltype = AA  length = 104
FEATURE                 Location/Qualifiers
REGION                  1..104
                        note = Description of Artificial Sequence:
                        Syntheticpolypeptide
source                  1..104
                        mol_type = protein
                        organism = synthetic construct
SEQUENCE: 5
SYELTQPPSV SVSPGQTASI TCSGDKLGDK YAVWYQQKPG QSPVLVIYQD SKRPSGIPER    60
FSGSNSGNTA TLTISGTQAM DEADYYCQAW EQEAAWVFGG GTKL                    104

SEQ ID NO: 6            moltype = AA  length = 11
FEATURE                 Location/Qualifiers
REGION                  1..11
                        note = Description of Artificial Sequence: Syntheticpeptide
```

```
source              1..11
                    mol_type = protein
                    organism = synthetic construct
SEQUENCE: 6
SGDKLGDKYA V                                                        11

SEQ ID NO: 7        moltype = AA  length = 7
FEATURE             Location/Qualifiers
REGION              1..7
                    note = Description of Artificial Sequence: Syntheticpeptide
source              1..7
                    mol_type = protein
                    organism = synthetic construct
SEQUENCE: 7
QDSKRPS                                                             7

SEQ ID NO: 8        moltype = AA  length = 10
FEATURE             Location/Qualifiers
REGION              1..10
                    note = Description of Artificial Sequence: Syntheticpeptide
source              1..10
                    mol_type = protein
                    organism = synthetic construct
SEQUENCE: 8
QAWEQEAAWV                                                          10
```

HUMAN ANTI-SEMAPHORIN 4D ANTIBODY

CROSS-REFERENCE TO RELATED APPLICATIONS

This application is a continuation of U.S. nonprovisional patent application Ser. No. 16/611,209 filed Nov. 5, 2019, which is a U.S. national stage filing under 35 U.S.C. § 371 of International Application No. PCT/US2018/031263, filed May 4, 2018, which claims the benefit of and priority under 35 U.S.C. § 119 to U.S. provisional patent application Ser. No. 62/501,981, filed May 5, 2017, the entirety of which applications are incorporated by reference herein for all purposes.

REFERENCE TO AN ELECTRONIC SEQUENCE LISTING

The contents of the electronic sequence listing (85550014C_SL.xml; Size: 11,000 bytes; and Date of Creation: Jul. 19, 2022) is herein incorporated by reference in its entirety.

BACKGROUND

Semaphorin 4D (SEMA4D), also known as CD100, is a transmembrane protein that belongs to the semaphorin gene family. SEMA4D is expressed on the cell surface as a homodimer, but upon cell activation SEMA4D can be released from the cell surface via proteolytic cleavage to generate sSEMA4D, a soluble form of the protein, which is also biologically active. See Suzuki et al., Nature Rev. Immunol. 3:159-167 (2003); Kikutani et al., Nature Immunol. 9:17-23 (2008).

SEMA4D is expressed at high levels in lymphoid organs, including the spleen, thymus, and lymph nodes, and in non-lymphoid organs, such as the brain and kidney. In lymphoid organs, SEMA4D is abundantly expressed on resting T cells but only weakly expressed on resting B cells and antigen-presenting cells (APCs), such as dendritic cells (DCs). Its expression, however, is upregulated in these cells following activation by various immunological stimuli. The release of soluble SEMA4D from immune cells is also increased by cell activation.

SEMA4D has been implicated in the development of certain cancers (Ch'ng et al., Cancer 110:164-72 (2007); Campos et al., Oncology Letters 5:1527-35 (2013); Kato et al., Cancer Sci. 102:2029-37 (2011)) and several reports suggest that one mechanism of this influence is the role of SEMA4D in promoting tumor angiogenesis (Conrotto et al., Blood 105:4321-4329 (2005). Basile et al., J Biol. Chem. 282: 34888-34895 (2007); Sierra et. al. J Exp. Med. 205: 1673 (2008); Zhou et al., Angiogenesis 15:391-407 (2012)). Tumor growth and metastasis involve a complex process of cross talk amongst the tumor cells, stroma and immune infiltrate, as well as the endothelial cells and vasculature. SEMA4D is over-expressed in a wide array of tumor types and is also produced by inflammatory cells recruited to the tumor microenvironment. Recent work suggests that SEMA4D plays a role in migration, survival, differentiation and organization of the different cell types that constitute the tumor stroma (Evans et al., Cancer Immunol. Res. 3:689-701 (2015)).

SEMA4D is implicated in neurodegenerative disorders, autoimmune diseases, demyelinating diseases, and cancer. In the central nervous system (CNS), SEMA4D is expressed on, e.g., infiltrating immune cells and oligodendrocyte precursor cells and its receptors are expressed on, e.g., neurons, oligodendrocytes, astrocytes, and endothelial cells (Okuno, T., et al., J. Immunol. 184:1499-1506 (2010)). SEMA4D can serve as an axonal guidance molecule (Swiercz et al., Neuron 35:51-63 (2002)) and can mediate GABAergic and glutamatergic synapse development (Paradis et al., Neuron 53:217-232 (2007)) among other activities.

SEMA4D has also been shown to play a role in the migration and differentiation of neuronal and oligodendrocyte precursor cells, CNS inflammation, and neurodegeneration. For example, SEMA4D-deficient mice are resistant to the development of experimental autoimmune encephalomyelitis (EAE) (Kumanogoh A et al., Immunity 13:621-631 (2000)), and blockade of SEMA4D can inhibit microglial activation and neuroinflammation in EAE (Okuno, T., et al., J. Immunol. 184:1499-1506 (2010)). Similarly, SEMA4D stimulation of endothelial cells can lead to production of the pro-inflammatory cytokine IL-8 (Yang, Y H et al., PLoS One 6:e25826 (2011)).

Recent publications have demonstrated the efficacy of anti-SEMA4D binding molecules, e.g., antibodies or antigen-binding fragments thereof in treating both cancer and neuroinflammatory/neurodegenerative diseases. For example, recent phase I clinical trials with the anti-SEMA4D antibody VX15/2503 demonstrated safety and efficacy in treating solid tumors. See, e.g., Patnaik, A., et al. Clin. Cancer Res. 22:827-836 (2016) and Southwell A L, et al., Neurobiol. Dis 76:46-56 (2015). There remains a need, however, for additional anti-SEMA4D antibodies with modified and/or improved profiles, e.g., with respect to binding characteristics, immunogenicity, and/or potency.

SUMMARY

This disclosure provides compositions and methods for treating diseases associated with semaphorin-4D (SEMA4D) pathology such as autoimmune diseases, inflammatory diseases, cancers, neuroinflammatory diseases and neurodegenerative disorders. According to aspects of the disclosure illustrated herein, there is provided antibodies or antigen-binding fragments thereof that specifically bind to SEMA4D. According to other aspects of the disclosure illustrated herein, there is provided a method for treating a subject with an autoimmune disease, inflammatory disease, cancer, neuroinflammatory disease, and neurodegenerative disorder including administering to the subject an effective amount of an antibody or antigen-binding fragment which specifically binds to SEMA4D and neutralizes SEMA4D activity.

In certain aspects, the antibody or antigen-binding fragment thereof that specifically binds to SEMA4D includes a heavy chain variable region (VH) and a light chain variable region (VL); wherein the VH includes complementarity determining regions (HCDRs) HCDR1, HCDR2, and HCDR3 that includes amino acid sequences identical or identical except for one, two, three, or four amino acid substitutions in one, two, or all three of the HCDRs to SEQ ID NO: 2, SEQ ID NO: 3, and SEQ ID NO: 4, respectively; and wherein the VL includes complementarity determining regions (LCDRs) LCDR1, LCDR2, and LCDR3 that includes amino acid sequences identical or identical except for one, two, three, or four amino acid substitutions in one, two, or all three of the LCDRs to SEQ ID NO: 6, SEQ ID NO: 7, and SEQ ID NO: 8, respectively.

In certain aspects, the anti-SEMA4D antibody or antigen-binding fragment thereof includes VH complementarity determining regions HCDR1, HCDR2, and HCDR3 that includes amino acid sequences identical to SEQ ID NO: 2, SEQ ID NO: 3, and SEQ ID NO: 4, respectively, and VL complementarity determining regions LCDR1, LCDR2, and LCDR3 that includes amino acid sequences identical to SEQ ID NO: 6, SEQ ID NO: 7, and SEQ ID NO: 8, respectively.

In certain aspects, the anti-SEMA4D antibody or antigen-binding fragment thereof includes a VH that includes framework regions (HFWs) HFW1, HFW2, HFW3, and HFW4, and the VL that includes framework regions (LFWs) LFW1, LFW2, LFW3, and LFW4. In certain aspects, the framework regions can be derived from a human antibody or from a non-human antibody.

In certain aspects, the anti-SEMA4D antibody or antigen-binding fragment thereof includes a VH that includes the amino acid sequence SEQ ID NO: 1. In certain aspects, the anti-SEMA4D antibody or antigen-binding fragment thereof includes a VL that includes the amino acid sequence SEQ ID NO: 5. In certain aspects, the anti-SEMA4D antibody or antigen-binding fragment thereof includes a VH and VL that includes amino acid sequence SEQ ID NO: 1 and SEQ ID NO: 5, respectively.

In certain aspects the VH of the anti-SEMA4D antibody or antigen-binding fragment thereof provided herein includes an amino acid sequence at least 80%, 85%, 90%, 95%, or 100% identical to SEQ ID NO: 1. In certain aspects, the VL of the anti-SEMA4D antibody or antigen-binding fragment thereof provided herein includes an amino acid sequence at least 80%, 85%, 90%, 95%, or 100% identical to SEQ ID NO: 5. In certain aspects the VH can include an amino acid sequence at least 80%, 85%, 90%, 95%, or 100% identical to SEQ ID NO: 1, and the VL can include an amino acid sequence at least 80%, 85%, 90%, 95%, or 100% identical to SEQ ID NO: 5.

In certain aspects, the anti-SEMA4D antibody or fragment thereof provided herein includes a heavy chain constant region or fragment thereof fused to the C-terminus of the VH. In certain aspects the heavy chain constant region or fragment thereof is a human heavy chain constant region. In certain aspects the heavy chain constant region or fragment thereof can be a human IgG4 constant region. In certain aspects the heavy chain constant region or fragment thereof is a non-human constant region. In certain aspects, the heavy chain constant region or fragment thereof is a murine IgG1 constant region. In certain aspects, the anti-SEMA4D antibody or fragment thereof includes a VH and VL, wherein the light chain constant region or fragment thereof is fused to the C-terminus of the VL. In certain aspects, the anti-SEMA4D antibody or fragment thereof provided herein includes a light chain constant region or fragment thereof fused to the C-terminus of the VL. In certain aspects the light chain constant region is a human light chain constant region, e.g., a human lambda or human kappa light chain constant region. In certain aspects the light chain constant region is a non-human light chain constant region, e.g., a murine lambda light chain constant region.

In certain aspects, the anti-SEMA4D antibody or fragment thereof provided herein can be an Fab fragment, an Fab' fragment, an F(ab')2 fragment, an Fd fragment, a single-chain Fv fragment (scFv), or a disulfide-linked Fv fragment (sdFv). In certain aspects the anti-SEMA4D antibody or fragment thereof can be multi-specific, e.g., bispecific.

In certain aspects, the anti-SEMA4D antibody or fragment thereof provided herein can specifically bind to human SEMA4D, mouse SEMA4D, rat SEMA4D, and/or non-human primate SEMA4D, e.g., cynomolgus monkey SEMA4D and/or marmoset SEMA4D. In certain aspects, the anti-SEMA4D antibody or fragment thereof provided herein can bind to SEMA4D, e.g., human SEMA4D, mouse SEMA4D, rat SEMA4D, and/or non-human primate SEMA4D, e.g., cynomolgus monkey SEMA4D and/or marmoset SEMA4D, with an affinity characterized by a dissociation constant KD no greater than 500 nM, 100 nM, 50.0 nM, 40.0 nM, 30.0 nM, 20.0 nM, 10.0 nM, 9.0 nM, 8.0 nM, 7.0 nM, 6.0 nM, 5.0 nM, 4.0 nM, 3.0 nM, 2.0 nM, 1.0 nM, 0.50 nM, 0.10 nM, 0.050 nM, 0.01 nM, 0.005 nM, or 0.001 nM In certain aspects, the anti-SEMA4D antibody or fragment thereof provided herein can inhibit SEMA4D from binding to a SEMA4D receptor, e.g., Plexin-B1, Plexin-B2, CD72, or any combination thereof.

In certain aspects, the anti-SEMA4D antibody or fragment thereof elicits minimal or no anti-antibody immune response upon administration to a subject.

In certain aspects, the anti-SEMA4D antibody or fragment thereof includes a heterologous moiety fused or conjugated thereto. In certain aspects, the heterologous moiety can be, e.g., a polypeptide, a cytotoxic agent, a therapeutic agent, a prodrug, a lipid, a carbohydrate, a nucleic acid, a detectable label, a polymer, or any combination thereof. In certain aspects, the heterologous moiety can include a binding molecule, an enzyme, a cytokine, a lymphokine, a hormonal peptide, or any combination thereof. In another aspect, the heterologous moiety can include a radionuclide, a biological toxin, an enzymatically active toxin, or any combination thereof. In another aspect, the heterologous moiety can include an enzyme, a fluorescent label, a chemiluminescent label, a bioluminescent label, a radioactive label, or any combination thereof.

In certain aspects, the disclosure provides a pharmaceutical composition that includes the anti-SEMA4D antibody or fragment thereof provided herein, and a carrier.

In certain aspects, the disclosure provides an isolated polynucleotide or combination of polynucleotides that includes one or more nucleic acid sequences encoding the anti-SEMA4D antibody or fragment thereof. In another aspect, the polynucleotide or combination of polynucleotides includes a nucleic acid sequence that encodes the VH of the anti-SEMA4D antibody or fragment thereof. In another aspect, the polynucleotide or combination of polynucleotides includes a nucleic acid sequence that encodes the VL of the anti-SEMA4D antibody or fragment thereof. In another aspect, the polynucleotide or combination of polynucleotides includes a nucleic acid sequence that encodes the VH and VL of the anti-SEMA4D antibody or fragment thereof. In yet another aspect, the disclosure provides a vector that includes the polynucleotide that includes one or more nucleic acid sequences encoding the anti-SEMA4D antibody or fragment thereof. In another aspect, the disclosure provides a host cell that includes the vector. In another aspect, the disclosure provides a method of producing the anti-SEMA4D antibody or fragment thereof.

In a certain aspect of the provided method, the anti-SEMA4D antibody or antigen-binding fragment neutralizes SEMA4D in a human subject.

According to aspects illustrated herein, the disclosure provides a method for treating a subject with an autoimmune disease or disorder, an inflammatory disease or disorder, cancer, a neuroinflammatory disease or disorder, a neurodegenerative disease or disorder, or any combination thereof including administering to the subject an effective amount of an antibody or antigen-binding fragment which specifically binds to SEMA4D and neutralizes SEMA4D activity. In certain aspects, the neuroinflammatory disease or disorder is multiple sclerosis. In certain aspects, the neurodegenerative disease or disorder is stroke, Alzheimer's disease, Parkinson's disease, Huntington's disease, Down syndrome, ataxia, amyotrophic lateral sclerosis (ALS), frontotemporal dementia (FTD), HIV-related cognitive impairment, CNS Lupus, mild cognitive impairment, or a combination thereof. In certain aspects, the autoimmune disease or the inflammatory disease is arthritis. In certain aspects, the autoimmune disease or the inflammatory disease is rheumatoid arthritis.

BRIEF DESCRIPTION OF THE DRAWINGS/FIGURES

FIG. 1A compares binding of MAbD2517 and MAbVX15/2503 (both formulated in PBS) to human SEMA4D as measured by ELISA.

FIG. 1B compares binding of MAbD2517 and MAbVX15/2503 (both formulated in PBS) to cynomolgus monkey SEMA4D as measured by ELISA.

FIG. 1C compares binding of MAbD2517 and MAbVX15/2503 (both formulated in PBS) to marmoset SEMA4D as measured by ELISA.

FIG. 1D compares binding of MAbD2517 and MAbVX15/2503 (both formulated in PBS) to mouse SEMA4D as measured by ELISA.

FIG. 3C shows the frequency of tumor regressions in Balb/c mice treated with either control Mouse IgG1/2B8 or chimeric antibody MAbD2585.

DETAILED DESCRIPTION

Definitions

Figure 2A:
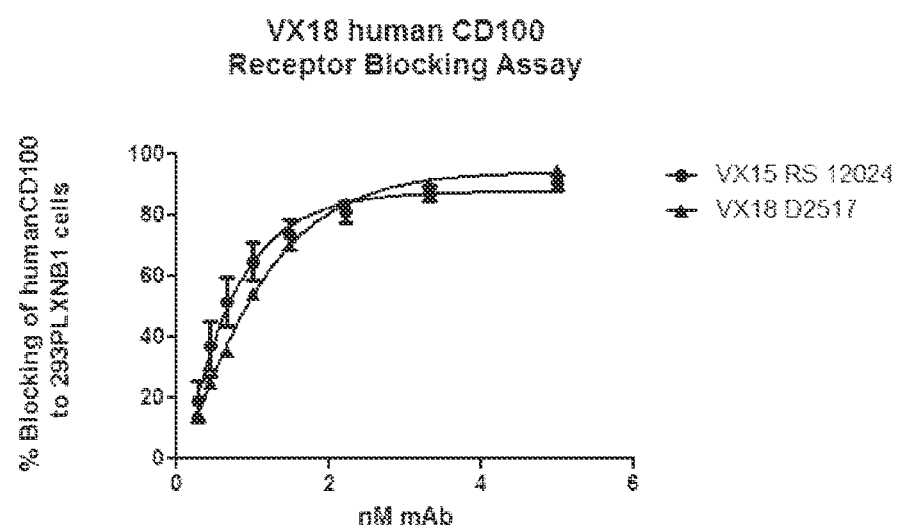
FIG. 2A shows the ability MAbD2517 to block human SEMA4D from binding to 293PLXNB1 cells as compared to MAbVX15/2503.
Figure 2B:
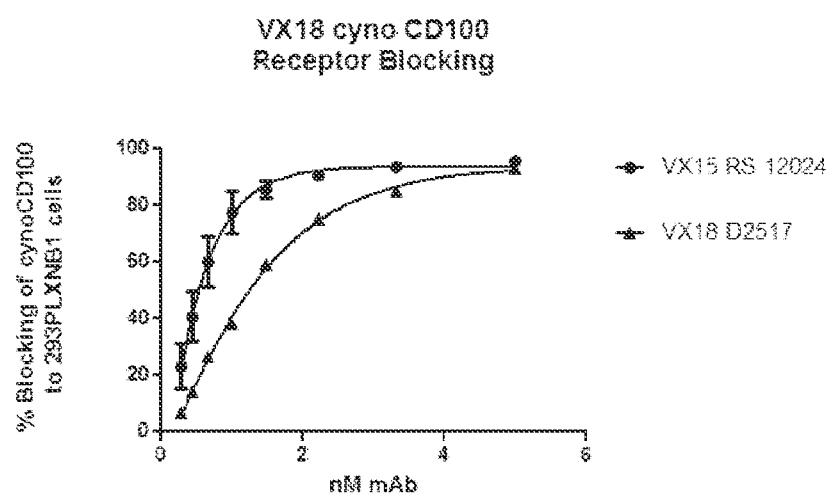
FIG. 2B shows the ability MAbD2517 to block cynomolgus monkey SEMA4D from binding to 293PLXNB1 cells as compared to MAbVX15/2503.
Figure 2C:
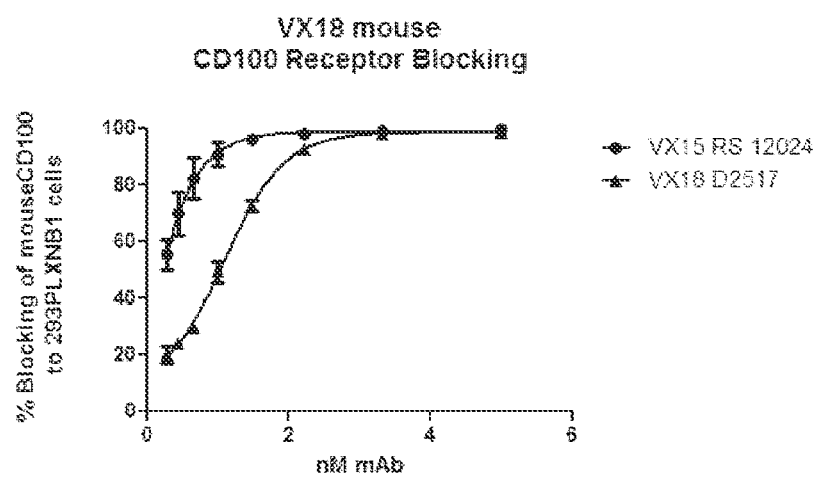
FIG. 2C shows the ability MAbD2517 to block mouse SEMA4D from binding to 293PLXNB1 cells as compared to MAbVX15/2503.
Figure 2D:
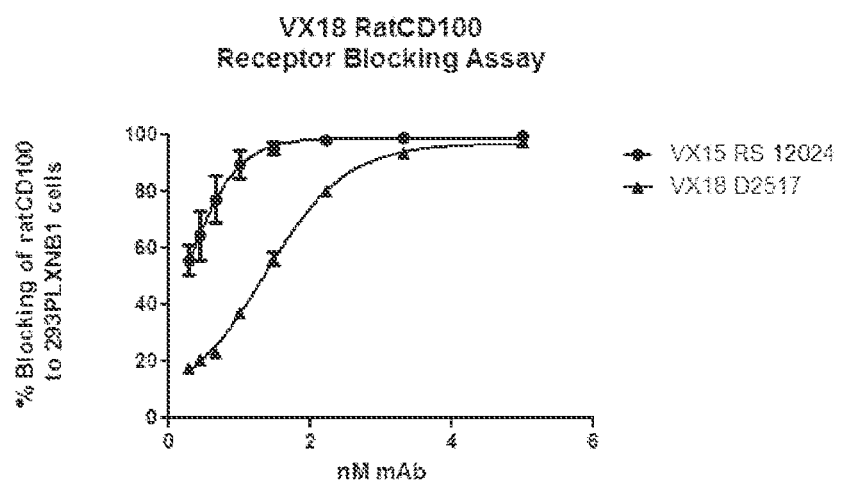
FIG. 2D shows the ability MAbD2517 to block rat SEMA4D from binding to 293PLXNB1 cells as compared to MAbVX15/2503.

It is to be noted that the term "a" or "an" entity refers to one or more of that entity; for example, "a binding molecule," is understood to represent one or more binding molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

Wherever embodiments are described with the language "comprising," otherwise analogous embodiments described in terms of "consisting of" and/or "consisting essentially of" are also provided.

Amino acids are referred to herein by their commonly known three letter symbols or by the one-letter symbols recommended by the IUPAC-IUB Biochemical Nomenclature Commission. Nucleotides, likewise, are referred to by their commonly accepted single-letter codes.

As used herein, the terms "cancer" and "cancerous" refer to or describe the physiological condition in mammals in which a population of cells are characterized by unregulated cell growth. Cancers can be categorized, e.g., as solid tumors or malignancies, or hematological cancers or malignancies. Both types can migrate to remote sites as metastases. A solid tumor can be categorized, e.g., as a sarcoma, a carcinoma, a melanoma, or a metastasis thereof.

"Tumor" and "neoplasm" as used herein refer to any mass of tissue that result from excessive cell growth or proliferation, either benign (noncancerous) or malignant (cancerous) including pre-cancerous lesions. In certain embodiments, tumors described herein express a SEMA4D receptor, e.g., Plexin-B1, Plexin-B2, and/or CD72, and/or can express SEMA4D.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, and derivatization by known protecting/ blocking groups, proteolytic cleavage, or modification by non-naturally occurring amino acids. A polypeptide can be derived from a biological source or produced by recombinant technology but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides which do not possess a defined three-dimensional structure, but rather can adopt many different conformations and are referred to as unfolded. As used herein, the term glycoprotein refers to a protein coupled to at least one carbohydrate moiety that is attached to the protein via an oxygen-containing or a nitrogen-containing side chain of an amino acid, e.g., a serine or an asparagine.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides which have been separated, fractionated, or partially or substantially purified by any suitable technique.

As used herein, the term "a non-naturally occurring polypeptide" or any grammatical variants thereof, is a conditional definition that explicitly excludes, but only excludes, those forms of the polypeptide that are, or might be, determined or interpreted by a judge or an administrative or judicial body, to be "naturally-occurring."

Other polypeptides disclosed herein are fragments, derivatives, analogs, or variants of the foregoing polypeptides, and any combination thereof. The terms "fragment," "variant," "derivative" and "analog" as disclosed herein include any polypeptides which retain at least some of the properties of the corresponding native antibody or polypeptide, for example, specifically binding to an antigen. Fragments of polypeptides include, for example, proteolytic fragments, as well as deletion fragments, in addition to specific antibody fragments discussed elsewhere herein. Variants of, e.g., a polypeptide include fragments as described above, and also polypeptides with altered amino acid sequences due to amino acid substitutions, deletions, or insertions. In certain aspects, variants can be non-naturally occurring. Non-naturally occurring variants can be produced using art-known mutagenesis techniques. Variant polypeptides can comprise conservative or non-conservative amino acid substitutions, deletions or additions. Derivatives are polypeptides that have been altered so as to exhibit additional features not found on the original polypeptide. Examples include fusion proteins. Variant polypeptides can also be referred to herein as "polypeptide analogs." As used herein a "derivative" of a polypeptide can also refer to a subject polypeptide having one or more amino acids chemically derivatized by reaction of a functional side group. Also included as "derivatives" are those peptides that contain one or more derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the present disclosure do not abrogate the binding of the polypeptide or antibody containing the amino acid sequence, to the antigen to which the binding molecule binds. Methods of identifying nucleotide and amino acid conservative substitutions which do not eliminate antigen-binding are well-known in the art (see, e.g., Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997)).

The term "polynucleotide" is intended to encompass a singular nucleic acid as well as plural nucleic acids, and refers to an isolated nucleic acid molecule or construct, e.g., messenger RNA (mRNA), cDNA, or plasmid DNA (pDNA). A polynucleotide can comprise a conventional phosphodiester bond or a non-conventional bond (e.g., an amide bond, such as found in peptide nucleic acids (PNA)). The terms "nucleic acid" or "nucleic acid sequence" refer to any one or more nucleic acid segments, e.g., DNA or RNA fragments, present in a polynucleotide.

By an "isolated" nucleic acid or polynucleotide is intended any form of the nucleic acid or polynucleotide that is separated from its native environment. For example, gel-purified polynucleotide, or a recombinant polynucleotide encoding a polypeptide contained in a vector would be considered to be "isolated." Also, a polynucleotide segment, e.g., a PCR product, which has been engineered to have restriction sites for cloning is considered to be "isolated." Further examples of an isolated polynucleotide include recombinant polynucleotides maintained in heterologous host cells or purified (partially or substantially) polynucleotides in a non-native solution such as a buffer or saline. Isolated RNA molecules include in vivo or in vitro RNA transcripts of polynucleotides, where the transcript is not one that would be found in nature. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, the term "a non-naturally occurring polynucleotide" or any grammatical variants thereof, is a conditional definition that explicitly excludes, but only excludes, those forms of the nucleic acid or polynucleotide that are, or might be, determined or interpreted by a judge, or an administrative or judicial body, to be "naturally-occurring."

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can include heterologous coding regions, either fused or unfused to another coding region. Heterologous coding regions include without limitation, those encoding specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA in predetermined cells. Other transcription control elements, besides a promoter, for example enhancers, operators, repressors, and transcription termination signals, can be operably associated with the polynucleotide to direct cell-specific transcription.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit B-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA), transfer RNA, or ribosomal RNA.

Polynucleotide and nucleic acid coding regions can be associated with additional coding regions which encode secretory or signal peptides, which direct the secretion of a polypeptide encoded by a polynucleotide as disclosed herein. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells can have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

Disclosed herein are certain binding molecules, or antigen-binding fragments, variants, or derivatives thereof Unless specifically referring to full-sized antibodies, the term "binding molecule" encompasses full-sized antibodies as well as antigen-binding subunits, fragments, variants, analogs, or derivatives of such antibodies, e.g., engineered antibody molecules or fragments that bind antigen in a manner similar to antibody molecules, but which use a different scaffold.

As used herein, the term "binding molecule" refers in its broadest sense to a molecule that specifically binds to a receptor, e.g., an epitope or an antigenic determinant. As described further herein, a binding molecule can comprise one of more "antigen binding domains" described herein. A non-limiting example of a binding molecule is an antibody or fragment thereof that retains antigen-specific binding.

As used herein, the terms "binding domain" or "antigen binding domain" refer to a region of a binding molecule that is necessary and sufficient to specifically bind to an epitope. For example, an "Fv," e.g., a variable heavy chain and variable light chain of an antibody, either as two separate polypeptide subunits or as a single chain, is considered to be a "binding domain." Other binding domains include, without limitation, the variable heavy chain (VHH) of an antibody derived from a camelid species, or six immunoglobulin complementarity determining regions (CDRs) expressed in a fibronectin scaffold. A "binding molecule" as described herein can include one, two, three, four, five, six, seven, eight, nine, ten, eleven, twelve or more "antigen binding domains."

The terms "antibody" and "immunoglobulin" can be used interchangeably herein. An antibody (or a fragment, variant, or derivative thereof as disclosed herein) includes at least the variable region of a heavy chain (for camelid species) or at least the variable region of a heavy chain and a light chain Basic immunoglobulin structures in vertebrate systems are relatively well understood. See, e.g., Harlow et al., Antibodies: A Laboratory Manual, (Cold Spring Harbor Laboratory Press, 2nd ed. 1988). Unless otherwise stated, the term "antibody" encompasses anything ranging from a small antigen-binding fragment of an antibody to a full sized antibody, e.g., an IgG antibody that includes two complete heavy chains and two complete light chains, an IgA antibody that includes four complete heavy chains and four complete light chains and optionally includes a J chain and/or a secretory component, or an IgM antibody that includes ten or twelve complete heavy chains and ten or twelve complete light chains and optionally includes a J chain.

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4 or α1-α2). It is the nature of this chain that determines the "class" of the antibody as IgG, IgM, IgA IgG, or IgE, respectively. The immunoglobulin subclasses (isotypes) e.g., IgGi, IgG2, IgG3, IgG4, IgA$_1$, IgA$_2$, etc. are well characterized and are known to confer functional specialization. Modified versions of each of these classes and isotypes are readily discernible to the skilled artisan in view of the instant disclosure and, accordingly, are within the scope of this disclosure.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. The basic structure of certain antibodies, e.g., IgG antibodies, includes two heavy chain subunits and two light chain subunits covalently connected via disulfide bonds to form a "Y" structure, also referred to herein as an "H2L2" structure.

Both the light and heavy chains are divided into regions of structural and functional homology. The terms "constant" and "variable" are used functionally. In this regard, it will be appreciated that the variable regions of both the variable light (VL) and variable heavy (VH) chain portions determine antigen recognition and specificity. Conversely, the constant regions of the light chain (CL) and the heavy chain (CH1, CH2 or CH3) confer biological properties such as secretion, transplacental mobility, Fc receptor binding, complement binding, and the like. By convention the numbering of the constant regions increases as they become more distal from the antigen binding site or amino-terminus of the antibody. The N-terminal portion is a variable region and at the C-terminal portion is a constant region; the CH3 (or CH4 in the case of IgM) and CL domains actually comprise the carboxy-terminus of the heavy and light chain, respectively.

As indicated above, a variable region (i.e., the "binding domain") allows the binding molecule to selectively recognize and specifically bind epitopes on antigens. That is, the VL region and VH region, or subset of the complementarity determining regions (CDRs), of a binding molecule, e.g., an antibody combine to form the variable region that defines a three-dimensional antigen binding site. More specifically, the antigen binding site is defined by three CDRs on each of the VH and VL chains. Certain antibodies form larger structures. For example, IgA can form a molecule that includes two H2L2 units, a J chain, and a secretory component, all covalently connected via disulfide bonds, and IgM can form a pentameric or hexameric molecule that includes five or six H2L2 units and optionally a J chain covalently connected via disulfide bonds.

The six "complementarity determining regions" or "CDRs" present in an antibody antigen-binding domain are short, non-contiguous sequences of amino acids that are specifically positioned to form the binding domain as the antibody assumes its three-dimensional configuration in an aqueous environment. The remainder of the amino acids in the binding domain, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The binding domain formed by the positioned CDRs defines a surface complementary to the epitope on the immunoreactive antigen. This complementary surface promotes the non-covalent binding of the antibody to its cognate epitope. The amino acids that make up the CDRs and the framework regions, respectively, can be readily identified for any given heavy or light chain variable region by one of ordinary skill in the art, since they have been defined in various different ways (see, "Sequences of Proteins of Immunological Interest," Kabat, E., et al., U.S. Department of Health and Human Services, (1983); and Chothia and Lesk, J. Mol. Biol., 196:901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. These particular regions have been described, for example, by Kabat et al., U.S. Dept. of Health and Human Services, "Sequences of Proteins of Immunological Interest" (1983) and by Chothia et al., J. Mol. Biol. 196:901-917 (1987), which are incorporated herein by reference. The Kabat and Chothia definitions include overlapping or subsets of amino acids when compared against each other. Nevertheless, application of either definition (or other definitions known to those of ordinary skill in the art) to refer to a CDR of an antibody or variant thereof is intended to be within the scope of the term as defined and used herein, unless otherwise indicated. The appropriate amino acids which encompass the CDRs as defined by each of the above cited references are set forth below in Table 1 as a comparison. The exact amino acid numbers which encompass a particular CDR will vary depending on the sequence and size of the CDR. Those skilled in the art can routinely determine which amino acids comprise a particular CDR given the variable region amino acid sequence of the antibody.

TABLE 1

CDR Definitions[1]

| Kabat | | Chothia |
| --- | --- | --- |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Rabat et al. (see below).

Immunoglobulin variable regions can also be analyzed using the IMGT information system (wwww://imgt.cines.fr/) (IMGT®/V-Quest) to identify variable region segments, including CDRs. See, e.g., Brochet, X. et al., Nucl. Acids Res. 36:W503-508 (2008).

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless use of the Kabat numbering system is explicitly noted, however, consecutive numbering is used for all amino acid sequences in this disclosure.

Binding molecules, e.g., antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH region, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

A binding molecule, e.g., an antibody or fragment, variant, or derivative thereof disclosed herein can be said to bind a target antigen with an off rate (k(off)) of less than or equal to $5\times10^{-2}$ sec$^{-1}$, $10^{-2}$ sec$^{-1}$, $5\times10^{-3}$ sec$^{-1}$, $10^{-3}$ sec$^{-1}$, $5\times10'$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$, $5\times10^{-7}$ sec$^{-1}$, or $10^{-7}$ sec$^{-1}$.

A binding molecule, e.g., an antibody or antigen-binding fragment, variant, or derivative disclosed herein can be said to bind a target antigen with an on rate (k(on)) of greater than or equal to $10^3 M^{-1}$ sec$^{-1}$, $5\times10^3 M^{-1}$ sec$^{-1}$, $10^4 M^{-1}$ sec$^{-1}$, $5\times10^4 M^{-1}$ sec$^{-1}$, $10^5 M^{-1}$ sec$^{-1}$, $5\times10^5 M^{-1}$ sec$^{-1}$, $10^6 M^{-1}$ sec$^{-1}$, or $5\times10^6 M^{-1}$ sec$^{-1}$, or $10^7 M^{-1}$ sec$^{-1}$.

A binding molecule, e.g., an antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope by at least 90%, at least 80%, at least 70%, at least 60%, or at least 50%.

As used herein, the term "affinity" refers to a measure of the strength of the binding of an individual epitope with one or more binding domains, e.g., of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of binding domains and an antigen. See, e.g., Harlow at pages 29-34. Avidity is related to both the affinity of individual binding domains in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a bivalent monoclonal antibody with a receptor present at a high density on a cell surface would also be of high avidity.

Binding molecules or antigen-binding fragments, variants or derivatives thereof as disclosed herein can also be described or specified in terms of their cross-reactivity. As used herein, the term "cross-reactivity" refers to the ability of a binding molecule, e.g., an antibody or fragment, variant, or derivative thereof, specific for one antigen, to react with a second antigen; a measure of relatedness between two different antigenic substances. Thus, a binding molecule is cross reactive if it binds to an epitope other than the one that induced its formation. The cross-reactive epitope generally contains many of the same complementary structural features as the inducing epitope, and in some cases, can actually fit better than the original.

A binding molecule, e.g., an antibody or fragment, variant, or derivative thereof can also be described or specified in terms of their binding affinity to an antigen. For example, a binding molecule can bind to an antigen with a dissociation constant or $K_D$ no greater than $5\times10^{-2}M$, $10^{-2}M$, $5\times10^{-3}M$, $10^{-3}$ M, $5\times10^{-4}M$, $10^{-4}M$, $5\times10^{-5}M$, $10^{-5}M$, $5\times10^{-6}M$, $10^{-6}M$, $5\times10^{-7}M$, $10^{-7}M$, $5\times10^{-8}M$, $10^{-8}M$, $5\times10^{-9}M$, $10^{-9}M$, $5\times10^{-10}M$, $10^{-10}$ M, $5\times10^{-11}$ M, $10^{-11}M$, $5\times10^{-12}M$, $10^{-12}M$, $5\times10^{-13}M$, $10^-M$, $5\times10^{-14}M$, $10^{-14}M$, $5\times10^{\times}_{15}M$, or $10^{\times15}M$.

Antibody fragments including single-chain antibodies or other binding domains can exist alone or in combination with one or more of the following hinge region, CH1, CH2, CH3, or CH4 domains, J chain, or secretory component. Also included are antigen-binding fragments that can include any combination of variable region(s) with one or more of a hinge region, CH1, CH2, CH3, or CH4 domains, a J chain, or a secretory component. Binding molecules, e.g., antibodies, or antigen-binding fragments thereof can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and can in some instances express endogenous immunoglobulins and some not, as described infra and, for example in, U.S. Pat. No. 5,939,598 by Kucherlapati et al.

As used herein, the term "heavy chain subunit" includes amino acid sequences derived from an immunoglobulin heavy chain, a binding molecule, e.g., an antibody comprising a heavy chain subunit includes at least one of: a VH region, a CH1 domain, a hinge (e.g., upper, middle, and/or lower hinge region) domain, a CH2 domain, a CH3 domain, a CH4 domain, or a variant or fragment thereof. For example, a binding molecule, e.g., an antibody or fragment, variant, or derivative thereof can include, in addition to a VH region, a CH1 domain; CH1 domain, a hinge, and a CH2 domain; a CH1 domain and a CH3 domain; a CH1 domain, a hinge, and a CH3 domain; or a CH1 domain, a hinge domain, a CH2 domain, and a CH3 domain. In certain aspects a binding molecule, e.g., an antibody or fragment, variant, or derivative thereof can include, in addition to a VH region, a CH3 domain and a CH4 domain; or a CH3 domain, a CH4 domain, and a J chain. Further, a binding molecule for use in the disclosure can lack certain constant region portions, e.g., all or part of a CH2 domain. It will be understood by one of ordinary skill in the art that these domains (e.g., the heavy chain subunit) can be modified such that they vary in amino acid sequence from the original immunoglobulin molecule.

The heavy chain subunits of a binding molecule, e.g., an antibody or fragment thereof, can include domains derived from different immunoglobulin molecules. For example, a heavy chain subunit of a polypeptide can include a CH1 domain derived from an IgG1 molecule and a hinge region derived from an IgG3 molecule. In another example, a heavy chain subunit can include a hinge region derived, in part, from an IgG1 molecule and, in part, from an IgG3 molecule. In another example, a heavy chain subunit can comprise a chimeric hinge derived, in part, from an IgG1 molecule and, in part, from an IgG4 molecule.

As used herein, the term "light chain subunit" includes amino acid sequences derived from an immunoglobulin light chain. The light chain subunit includes at least one of a VL or CL (e.g., Cκ or Cλ) domain.

Binding molecules, e.g., antibodies or antigen-binding fragments, variants, or derivatives thereof can be described or specified in terms of the epitope(s) or portion(s) of an antigen that they recognize or specifically bind. The portion of a target antigen that specifically interacts with the antigen binding domain of an antibody is an "epitope," or an "antigenic determinant." A target antigen can comprise a single epitope or at least two epitopes, and can include any number of epitopes, depending on the size, conformation, and type of antigen.

As previously indicated, the subunit structures and three-dimensional configuration of the constant regions of the various immunoglobulin classes are well known. As used herein, the term "VH region" includes the amino terminal variable region of an immunoglobulin heavy chain and the term "CH1 domain" includes the first (most amino terminal) constant region domain of an immunoglobulin heavy chain. The CH1 domain is adjacent to the VH region and is amino terminal to the hinge region of a typical immunoglobulin heavy chain molecule.

As used herein the term "CH2 domain" includes the portion of a heavy chain molecule that extends, e.g., from about amino acid 244 to amino acid 360 of an IgG antibody using conventional numbering schemes (amino acids 244 to 360, Kabat numbering system; and amino acids 231-340), EU numbering system; see Kabat E A et al. op. cit. The CH3 domain extends from the CH2 domain to the C-terminal of the IgG molecule and comprises approximately 108 amino acids. Certain immunoglobulin classes, e.g., IgM, further include a CH4 region.

As used herein, the term "hinge region" includes the portion of a heavy chain molecule that joins the CH1 domain to the CH2 domain. This hinge region comprises approximately 25 amino acids and is flexible, thus allowing the two N-terminal antigen binding regions to move independently.

As used herein the term "disulfide bond" includes the covalent bond formed between two sulfur atoms. The amino acid cysteine comprises a thiol group that can form a disulfide bond or bridge with a second thiol group. In certain IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" refers to an antibody in which the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The terms "multispecific antibody, or "bispecific antibody" refer to an antibody that has binding domains for two or more different epitopes within a single antibody molecule. Other binding molecules in addition to the canonical antibody structure can be constructed with two binding specificities. Epitope binding by bispecific or multispecific antibodies can be simultaneous or sequential. Triomas and hybrid hybridomas are two examples of cell lines that can secrete bispecific antibodies. Bispecific antibodies can also be constructed by recombinant means. (Ströhlein and Heiss, Future Oncol. 6:1387-94 (2010); Mabry and Snavely, IDrugs. 13:543-9 (2010)). A bispecific antibody can also be a diabody.

As used herein, the term "engineered antibody" refers to an antibody in which the variable region in either the heavy and light chain or both is altered by at least partial replacement of one or more amino acids in either the CDR or framework regions. In certain aspects entire CDRs from an antibody of known specificity can be grafted into the framework regions of a heterologous antibody. Although alternate CDRs can be derived from an antibody of the same class or even subclass as the antibody from which the framework regions are derived, CDRs can also be derived from an antibody of different class, e.g., from an antibody from a different species. An engineered antibody in which one or more "donor" CDRs from a non-human antibody of known specificity are grafted into a human heavy or light chain framework region is referred to herein as a "humanized antibody." In certain aspects, not all of the CDRs are replaced with the complete CDRs from the donor variable region and yet the antigen binding capacity of the donor can still be transferred to the recipient variable regions. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" or other grammatical equivalents can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the translational reading frame of the original ORFs. Thus, a recombinant fusion protein is a single protein containing two or more segments that correspond to polypeptides encoded by the original ORFs (which segments are not normally so joined in nature.)

Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which amino acids that neighbor each other in the sequence are contiguous in the primary structure of the polypeptide. A portion of a polypeptide that is "amino-terminal" or "N-terminal" to another portion of a polypeptide is that portion that comes earlier in the sequential polypeptide chain. Similarly, a portion of a polypeptide that is "carboxy-terminal" or "C-terminal" to another portion of a polypeptide is that portion that comes later in the sequential polypeptide chain. For example, in a typical antibody, the variable region is "N-terminal" to the constant region, and the constant region is "C-terminal" to the variable region.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "anti-SEMA4D binding molecule" refers to a molecule that specifically binds to SEMA4D, e.g., an antibody or antigen-binding fragment, variant, or derivative thereof. Unless specifically referring to full-sized antibodies such as naturally occurring antibodies, the term "anti-SEMA4D antibody" encompasses full-sized antibodies as well as antigen-binding fragments as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

Terms such as "treating" or "treatment" or "to treat" or "alleviating" or "to alleviate" refer to therapeutic measures that cure, slow down, lessen symptoms of, and/or halt or slow the progression of an existing diagnosed pathologic condition or disorder. Terms such as "prevent," "prevention," "avoid," "deterrence" and the like refer to prophylactic or preventative measures that prevent the development of an undiagnosed targeted pathologic condition or disorder. Thus, "those in need of treatment" can include those already with the disorder; those prone to have the disorder; and those in whom the disorder is to be prevented. As used herein, phrases such as "a subject that would benefit from therapy" and "an animal in need of treatment" includes subjects, such as mammalian subjects, that would benefit from administration of a therapy as described herein.

The term "therapeutically effective amount" refers to an amount of an antibody, polypeptide, polynucleotide, small organic molecule, or other drug effective to "treat" a disease or disorder in a subject or mammal.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, swine, cows, bears, and so on.

Target Polypeptide Description—SEMA4D

As used herein, the terms "semaphorin-4D", "SEMA4D", and "SEMA4D polypeptide" are used interchangeably, as are "SEMA4D" and "Sema4D." In certain embodiments, SEMA4D is expressed on the surface of or secreted by a cell. In another embodiment, SEMA4D is membrane bound. In another embodiment, SEMA4D is soluble, e.g., sSEMA4D. In another embodiment, SEMA4D can include a full-sized SEMA4D or a fragment thereof, or a SEMA4D variant polypeptide, where the fragment of SEMA4D or SEMA4D variant polypeptide retains some or all functional properties of the full-sized SEMA4D.

The full-sized human SEMA4D protein is a homodimeric transmembrane protein consisting of two polypeptide chains of 150 kDa. SEMA4D belongs to the semaphorin family of cell surface receptors and is also referred to as CD100. Both human and mouse SEMA4D/Sema4D can be proteolytically cleaved from their transmembrane form to generate 120-kDa soluble forms, giving rise to two Sema4D isoforms (Kumanogoh et al., J. Cell Science 116:3464 (2003)). Semaphorins consist of soluble and membrane-bound proteins that were originally defined as axonal-guidance factors which play an important role in establishing precise connections between neurons and their appropriate target. Structurally considered a class IV semaphorin, SEMA4D consists of an amino-terminal signal sequence followed by a characteristic 'Sema' domain, which contains 17 conserved cysteine residues, an Ig-like domain, a lysine-rich stretch, a hydrophobic transmembrane region, and a cytoplasmic tail.

The SEMA4D polypeptide includes a signal sequence of about 13 amino acids followed by a semaphorin domain of about 512 amino acids, an immunoglobulin-like (Ig-like) domain of about 65 amino acids, a lysine-rich stretch of 104 amino acids, a hydrophobic transmembrane region of about 19 amino acids, and a cytoplasmic tail of 110 amino acids. A consensus site for tyrosine phosphorylation in the cytoplasmic tail supports the predicted association of SEMA4D with a tyrosine kinase (Schlossman et al., Eds. (1995) Leucocyte Typing V (Oxford University Press, Oxford).

SEMA4D is known to have at least three functional receptors, Plexin-B1, Plexin-B2 and CD72. Plexin-B1, is expressed in non-lymphoid tissues and has been shown to be a high affinity (1 nM) receptor for SEMA4D (Tamagnone et al., Cell 99:71-80 (1999)). SEMA4D stimulation of Plexin-B 1 signaling has been shown to induce growth cone collapse of neurons, and to induce process extension collapse and apoptosis of oligodendrocytes (Giraudon et al., J. Immunol. 172:1246-1255 (2004); Giraudon et al., Neuro-Molecular Med. 7:207-216 (2005)). After binding to SEMA4D, Plexin-B 1 signaling mediates the inactivation of R-Ras, leading to a decrease in the integrin mediated attachment to the extracellular matrix, as well as to activation of RhoA, leading to cell collapse by reorganization of the cytoskeleton (Kruger et al., Nature Rev. Mol. Cell Biol. 6:789-800 (2005); Pasterkamp, TRENDS in Cell Biology 15:61-64 (2005)). Plexin-B2 has an intermediate affinity for SEMA4D and a recent report indicates that Plexin-B2 is expressed on keratinocytes and activates SEMA4D-positive γδ cells to contribute to epithelial repair (Witherden et al., Immunity 37:314-25 (2012)).

In lymphoid tissues, CD72 is utilized as a low affinity (300 nM) SEMA4D receptor (Kumanogoh et al., Immunity 13:621-631 (2000)). B cells and Antigen Presenting Cells (APC) express CD72, and anti-CD72 antibodies have many of the same effects as sSEMA4D, such as enhancement of CD40-induced B cell responses and B cell shedding of CD23. CD72 is thought to act as a negative regulator of B cell responses by recruiting the tyrosine phosphatase SHP-1, which can associate with many inhibitory receptors. Interaction of SEMA4D with CD72 results in the dissociation of SHP-1, and the loss of this negative activation signal. SEMA4D has been shown to promote T cell stimulation and B cell aggregation and survival in vitro. The addition of SEMA4D-expressing cells or sSEMA4D enhances CD40-induced B cell proliferation and immunoglobulin production in vitro, and accelerates in vivo antibody responses (Ishida et al., Inter. Immunol. 15:1027-1034 (2003); Kumanogoh and H. Kukutani, Trends in Immunol. 22:670-676 (2001)). sSEMA4D enhances the CD40 induced maturation of DCs, including up-regulation of costimulatory molecules and increased secretion of IL-12. In addition, sSEMA4D can inhibit immune cell migration, which can be reversed by addition of blocking anti-SEMA4D mouse antibodies (Elhabazi et al., J. Immunol. 166:4341-4347 (2001); Delaire et al., J. Immunol. 166:4348-4354 (2001)).

Sema4D is expressed at high levels in lymphoid organs, including the spleen, thymus, and lymph nodes, and in non-lymphoid organs, such as the brain, heart, and kidney. In lymphoid organs, Sema4D is abundantly expressed on resting T cells but only weakly expressed on resting B cells and antigen-presenting cells (APCs), such as dendritic cells (DCs).

Cellular activation increases the surface expression of SEMA4D as well as the generation of soluble SEMA4D (sSEMA4D). The expression pattern of SEMA4D suggests that it plays an important physiological as well as pathological role in the immune system. SEMA4D has been shown to promote B cell activation, aggregation and survival; enhance CD40-induced proliferation and antibody production; enhance antibody response to T cell dependent antigens; increase T cell proliferation; enhance dendritic cell maturation and ability to stimulate T cells;

and is directly implicated in demyelination and axonal degeneration (Shi et al., Immunity 13:633-642 (2000); Kumanogoh et al., J. Immunol. 169:1175-1181 (2002); and Watanabe et al., J. Immunol. 167:4321-4328 (2001)).

Human Anti-SEMA4D Antibody

This disclosure provides an anti-SEMA4D binding molecule, e.g., an anti-SEMA4D binding molecule, e.g., antibody or antigen binding fragment, variant, or derivative thereof with a heavy chain variable region (VH) and a light chain variable region (VL) related to, or identical to the VH and VL comprising amino acid sequences SEQ ID NO: 1 and SEQ ID NO: 5, respectively. In certain aspects the provided binding molecule, e.g., antibody or antigen binding fragment, variant, or derivative thereof is fully human.

In certain aspects, the anti-SEMA4D binding molecule, e.g., antibody or antigen binding fragment, variant, or derivative thereof provided herein has VH and VL regions comprising amino acid sequences that has at least about 80%, about 85%, about 88%, about 89%, about 90%, about 91%, about 92%, about 93%, about 94%, about 95%, about 96%, about 97%, about 98%, about 99%, or 100% identical to the VH and VL regions of a reference anti-SEMA4D antibody molecule with VH and VL regions comprising the amino acid sequences SEQ ID NO: 1 and SEQ ID NO: 5, respectively.

In certain aspects, the anti-SEMA4D binding molecule, e.g., antibody or antigen binding fragment, variant, or derivative thereof can inhibit SEMA4D interaction with its receptor, e.g., Plexin-B1, Plexin-B2, or CD72. In certain aspects the anti-SEMA4D binding molecule, e.g., antibody or antigen binding fragment, variant, or derivative thereof can inhibit SEMA4D-mediated Plexin-B 1 signal transduction.

In certain aspects, the anti-SEMA4D binding molecule, e.g., antibody or antigen binding fragment, variant, or derivative thereof competitively inhibits a reference antibody comprising a variable heavy chain region (VH) comprising the amino acid sequence SEQ ID NO: 1 and a variable light chain region (VL) comprising the amino acid sequence SEQ ID NO: 5 from binding to SEMA4D. In certain aspects, the anti-SEMA4D binding molecule, e.g., antibody or antigen binding fragment, variant, or derivative thereof binds to the same SEMA4D epitope as a reference antibody comprising a VH comprising the amino acid sequence SEQ ID NO: 1 and a VL comprising the amino acid sequence SEQ ID NO: 5. In certain aspects, the VH of the anti-SEMA4D binding molecule, e.g., antibody or antigen binding fragment, variant, or derivative thereof comprises three complementarity determining regions (CDRs) HCDR1, HCDR2, and HCDR3, and the VL comprises three CDRs LCDR1, LCDR2, and LCDR3, the CDRs comprising the amino acid sequences SEQ ID NO: 2, SEQ ID NO: 3, SEQ ID NO: 4, SEQ ID NO: 6, SEQ ID NO: 7, and SEQ ID NO: 8, respectively except for at least one, two, three, four, five, or six single conservative amino acid substitutions in one or more of the CDRs. In certain aspects the CDRs comprise the amino acid sequences SEQ ID NO: 2, SEQ ID NO: 3, SEQ ID NO: 4, SEQ ID NO: 6, SEQ ID NO: 7, and SEQ ID NO: 8, respectively.

In certain aspects the VH of the anti-SEMA4D binding molecule, e.g., antibody or antigen binding fragment, variant, or derivative thereof comprises an amino acid sequence at least 70%, 75%, 80%, 85%, 90%, 95%, or 100% identical to SEQ ID NO: 1 and the VL of the anti-SEMA4D binding molecule, e.g., antibody or antigen binding fragment, variant, or derivative thereof comprises an amino acid sequence at least 70%, 75%, 80%, 85%, 90%, 95%, or 100% identical to SEQ ID NO: 5. In certain aspects, the VH comprises the amino acid sequence SEQ ID NO: 1 and the VL comprises the amino acid sequence SEQ ID NO: 5.

Also provided herein are polypeptides encoding anti-SEMA4D antibodies, or antigen-binding fragments, variants, or derivatives thereof as described herein, polynucleotides encoding such polypeptides, vectors comprising such polynucleotides, and host cells comprising such vectors or polynucleotides, for use, e.g., in producing an anti-SEMA4D binding molecule, e.g., antibody or antigen binding fragment, variant, or derivative thereof as provided herein.

Suitable biologically active variants of an anti-SEMA4D binding molecule, e.g., antibody or antigen binding fragment, variant, or derivative thereof are provided by this disclosure, and can be made and used according to methods provided herein or according to methods well known to those of ordinary skill in the art. Such variants retain certain desired binding properties of the reference anti-SEMA4D antibody provided herein. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, Proc. Natl. Acad. Sci. USA 82:488-492 (1985); Kunkel et al., Methods Enzymol. 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest can be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. In certain aspects, conservative substitutions, such as exchanging one amino acid with another having similar properties are used. Examples of conservative amino acid substitutions as taught by the PAM 250 matrix of the Dayhoff et al. model include, but are not limited to, Gly↔Ala, Val↔Ile↔Leu, Asp↔Glu, Lys↔Arg, Asn↔Gln, and Phe↔Trp↔Tyr.

In constructing variants of the anti-SEMA4D binding molecule, e.g., an antibody or antigen-binding fragment thereof, polypeptides of interest, modifications are made such that variants continue to possess the desired properties, e.g., being capable of specifically binding to SEMA4D, e.g., human SEMA4D, non-human primate SEMA4D (e.g., cynomolgus monkey, marmoset, and/or rhesus monkey SEMA4D), and/or rodent SEMA4D (e.g., mouse and/or rat SEMA4D), e.g., expressed on the surface of or secreted by a cell, where the binding molecule, e.g., antibody or fragment, variant, or derivative thereof has SEMA4D binding, receptor blocking, or neutralizing activity, as described herein. In certain aspects, mutations made in the DNA encoding the variant polypeptide maintain the reading frame and do not create complementary regions that could produce secondary mRNA structure. See EP Patent Application Publication No. 75,444.

Methods for measuring the binding specificity and/or activity of an anti-SEMA4D binding molecule, e.g., an antibody or antigen-binding fragment, variant, or derivative thereof include, but are not limited to, standard binding assays, including competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., Immunity 13:633-642 (2000); Kumanogoh et al., J. Immunol. 169:1175-1181 (2002); Watanabe et al., J. Immunol. 167:4321-4328 (2001); Wang et al., Blood 97:3498-3504 (2001); and Giraudon et al., J. Immunol. 172:1246-1255 (2004), all of which are herein incorporated by reference.

When discussed herein whether any particular polypeptide, including the constant regions, CDRs, VH regions, or VL regions disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide, the % identity can be determined using methods and computer programs/software known in the art. Optimal alignment of sequences for comparison can be conducted, for example, by a local homology algorithm (Smith & Waterman, Adv. Appl. Math. 2:482-489 (1981), by a global alignment algorithm (Needleman & Wunsch, J. Mol. Biol. 48:443 (1970), by search for similarity methods (Pearson & Lipman, Proc. Natl. Acad. Sci. U.S.A. 85:2444 (1988); Altschul et al., Nucl. Acids Res. 25:3389-402 (1997), by computerized implementations of these algorithms (e.g., GAP, BESTFIT, FASTA, and BLAST in the Wisconsin Genetics Software Package, Genetics Computer Group, 575 Science Dr., Madison, Wis.), typically using the default settings, or by manual alignment and visual inspection (see, e.g., Current Protocols in Molecular Biology, Ausubel et al. (eds.), 1994).

For purposes of the present disclosure, percent sequence identity can be determined using the Smith-Waterman homology search algorithm using a search with a gap open penalty of 12 and a gap extension penalty of 2, BLOSUM matrix of 62. A variant can, for example, differ from a reference anti-SEMA4D antibody (e.g., MAb 2517 provided herein) by as few as 1 to 15 amino acid residues, as few as 1 to 10 amino acid residues, such as 6-10, as few as 5, as few as 4, 3, 2, or even 1 amino acid residue.

In certain aspects, the disclosure provides an antibody or antigen-binding fragment, variant, or derivative thereof that specifically binds to SEMA4D, where the antibody or fragment thereof comprises a VH and a VL. In certain aspects the VH comprises complementarity determining regions (HCDRs) HCDR1, HCDR2, and HCDR3 comprising amino acid sequences identical or identical except for one, two, three, four, five, or six amino acid substitutions in one, two, or all three of the HCDRs to SEQ ID NO: 2, SEQ ID NO: 3, and SEQ ID NO: 4, respectively. In certain aspects the HCDR1, HCDR2, and HCDR3 comprise amino acid sequences identical to SEQ ID NO: 2, SEQ ID NO: 3, and SEQ ID NO: 4, respectively. In certain aspects the VL comprises complementarity determining regions (LCDRs) LCDR1, LCDR2, and LCDR3 comprising amino acid sequences identical or identical except for one, two, three, four, five, or six amino acid substitutions in one, two, or all three of the LCDRs to SEQ ID NO: 6, SEQ ID NO: 7, and SEQ ID NO: 8, respectively. In certain aspects the LCDR1, LCDR2, and LCDR3 comprise amino acid sequences identical to SEQ ID NO: 6, SEQ ID NO: 7, and SEQ ID NO: 8, respectively. In certain aspects, the VH further comprises framework regions (HFWs) HFW1, HFW2, HFW3, and HFW4, and the VL further comprises framework regions (LFWs) LFW1, LFW2, LFW3, and LFW4. In certain aspects, the framework regions are derived from a human antibody. In certain aspects, e.g., where the antibody is to be used in a non-human model system, the framework regions are derived from a non-human antibody, e.g., a mouse antibody. In certain aspects, the VH comprises the amino acid sequence SEQ ID NO: 1. In certain aspects, the VL comprises the amino acid sequence SEQ ID NO: 5.

In certain aspects the disclosure provides an antibody, e.g., a fully-human antibody, or an antigen-binding fragment, variant, or derivative thereof that specifically binds to semaphorin-4D (SEMA4D) comprising VH and a VL. In certain aspects the VH comprises an amino acid sequence at least 80%, 85%, 90%, 95%, 96%, 97%, 98%, 99%, or 100% identical to SEQ ID NO: 1. In certain aspects the VL comprises an amino acid sequence at least 80%, 85%, 90%, 95%, 96%, 97%, 98%, 99%, or 100% identical to SEQ ID NO: 5. In certain aspects, the VH comprises an amino acid sequence at least 80%, 85%, 90%, 95%, 96%, 97%, 98%, 99%, or 100% identical to SEQ ID NO: 1; and the VL comprises an amino acid sequence at least 80%, 85%, 90%, 95%, 96%, 97%, 98%, 99%, or 100% identical to SEQ ID NO: 5. In certain aspects the VH comprises the amino acid sequence SEQ ID NO: 1 and the VL comprises the amino acid sequence SEQ ID NO: 5. In certain aspects the VH and the VL are fully human.

In certain aspects, the anti-SEMA4D antibody or antigen-binding fragment, variant, or derivative thereof as provided herein can specifically bind to human SEMA4D, rodent SEMA4D, e.g., mouse SEMA4D and/or rat SEMA4D, and/or non-human primate SEMA4D, e.g., cynomolgus monkey SEMA4D and/or marmoset SEMA4D.

In certain aspects the antibody or fragment, variant, or derivative thereof further comprises a heavy chain constant region or fragment, variant, or derivative thereof fused to the C-terminus of the VH. The heavy chain constant region or fragment thereof can be derived from any species, but in certain aspects the heavy chain constant region or fragment, variant, or derivative thereof is, or is derived from a human heavy chain constant region, e.g., a human IgG1, IgG2, IgG3, IgG4, IgA, IgE, or IgM constant region. In certain aspects the heavy chain constant region is a human IgG4 constant region, or fragment, variant, or derivative thereof. In certain aspects, e.g., where the provided anti-SEMA4D antibody or fragment thereof is to be used in a non-human model system, the heavy chain constant region or fragment thereof can be a non-human heavy chain constant region, e.g., a murine heavy chain constant region such as a murine IgG1 constant region.

In certain aspects the antibody or fragment, variant, or derivative thereof further comprises a light chain constant region or fragment, variant, or derivative thereof fused to the C-terminus of the VL. The light chain constant region or fragment thereof can be derived from any species, but in certain aspects the light chain constant region or fragment thereof is derived from a human light chain constant region, e.g., a human kappa or lambda constant region. In certain aspects the light chain constant region or fragment, variant, or derivative thereof is, or is derived from a human lambda light chain constant region. In certain aspects the light chain constant region is a human lambda constant region. In certain aspects, e.g., where the provided anti-SEMA4D antibody or fragment thereof is to be used in a non-human model system, the light chain constant region or fragment thereof can be a non-human light chain constant region, e.g., a murine light chain constant region such as a murine lambda constant region.

In certain aspects the disclosure provides an anti-SEMA4D antibody fragment comprising VH and VL regions as described above. In certain aspects, the fragment can be, e.g., an Fab fragment, an Fab' fragment, an F(ab')2 fragment, an Fd fragment, a single-chain Fv fragment (scFv), or a disulfide-linked Fv fragment (sdFv).

In certain aspects, the anti-SEMA4D antibody or fragment, variant, or derivative thereof provided by this disclosure can be multispecific, e.g., bispecific. In addition to the binding properties of a SEMA4D antibody as provided herein, a multispecific antibody or fragment thereof as provided herein can bind to additional SEMA4D epitopes or can bind to other unrelated epitopes.

In certain aspects, an anti-SEMA4D antibody or fragment thereof as provided herein can specifically bind to SEMA4D, e.g., human SEMA4D, mouse SEMA4D, cynomolgus monkey SEMA4D, marmoset SEMA4D, or any combination thereof, with a binding affinity characterized by a dissociation constant KD no greater than 500 nM, 100 nM, 50.0 nM, 40.0 nM, 30.0 nM, 20.0 nM, 10.0 nM, 9.0 nM, 8.0 nM, 7.0 nM, 6.0 nM, 5.0 nM, 4.0 nM, 3.0 nM, 2.0 nM, 1.0 nM, 0.50 nM, 0.10 nM, 0.050 nM, 0.01 nM 0.005 nM, or 0.001 nM. Methods and devices for measuring the KD of an antibody or fragment thereof to SEMA 4D, such as BIA-CORE, are well known to those of ordinary skill in the art.

In certain aspects, the anti-SEMA4D antibody or fragment thereof provided by this disclosure can inhibit SEMA4D from binding to a SEMA4D receptor, e.g., Plexin-B1, Plexin-B2, and/or CD72.

In certain aspects, the anti-SEMA4D antibody or antigen-binding fragment, variant, or derivative thereof provided herein is fully human, and elicits minimal or no anti-antibody immune response upon administration to a human subject. Methods to measure anti-antibody immune responses in a subject are well known in the art. See, e.g., Darwish, I A, Int. J. Biomed. Sci. 2:217-235 (2006).

The constant region of an anti-SEMA4D antibody can be mutated to alter effector function in a number of ways. For example, see U.S. Pat. No. 6,737,056 B1 and U.S. Patent Application Publication No. 2004/0132101 A1, which disclose Fc mutations that optimize antibody binding to Fc receptors.

In certain anti-SEMA4D binding molecules, e.g., antibodies or fragments, variants or derivatives thereof provided herein, the Fc portion can be mutated to modulate, e.g., increase or decrease, effector function using techniques known in the art. For example, the deletion or inactivation (through point mutations or other means) of a constant region domain can reduce Fc receptor binding of the circulating modified antibody thereby increasing tumor localization. In other cases, constant region modifications consistent with the instant disclosure modulate complement binding and thus can increase or reduce the serum half-life. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well known immunological techniques without undue experimentation.

Anti-SEMA4D binding molecules, e.g., antibodies or fragments thereof provided herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-SEMA4D polypeptide, to block SEMA4D interaction with its receptor, or to inhibit, delay, or reduce metastases in a subject, e.g., a cancer patient).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage or improve a hybridoma's antibody production. Alternatively, non-neutral missense mutations can alter an antibody's ability to bind antigen. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein, (e.g., ability to immunospecifically bind at least one epitope of a SEMA4D polypeptide) can be determined using techniques described herein or by routinely modifying techniques known in the art.

In certain aspects, an anti-SEMA4D binding molecule, e.g., antibody or fragment thereof provided herein can comprise at least one optimized complementarity-determining region (CDR). By "optimized CDR" is intended that the CDR has been modified and optimized to improve binding affinity and/or anti-SEMA4D activity that is imparted to an anti-SEMA4D binding molecule comprising the optimized CDR. "Anti-SEMA4D activity" or "SEMA4D blocking activity" can include activity which modulates. e.g., reduces, eliminates, lessens, or prevents one or more SEMA4D activities. Non-limiting SEMA4D activities include: B cell activation, aggregation and survival; CD40-induced proliferation and antibody production; antibody response to T cell dependent antigens; T cell or other immune cell proliferation; dendritic cell maturation; demyelination and axonal degeneration; apoptosis of pluripotent neural precursors and/or oligodendrocytes; induction of endothelial cell migration; inhibition of spontaneous monocyte migration; promotion of tumor cell growth or metastasis, binding to cell surface plexin-B 1 or other receptor, or any other activity association with soluble SEMA4D or SEMA4D that is expressed on the surface of SEMA4D+ cells. In a particular embodiment, anti-SEMA4D activity includes the ability to inhibit, delay, or reduce tumor metastases, either in combination with inhibition, delay, or reduction of primary tumor cell growth and tumor metastases, or independently of primary tumor cell growth and tumor metastases. Anti-SEMA4D activity can also be attributed to a decrease in incidence or severity of diseases associated with SEMA4D expression, including, but not limited to, certain types of cancers including solid tumors and lymphomas, autoimmune diseases, inflammatory diseases including central nervous system (CNS) and peripheral nervous system (PNS) inflammatory diseases, neurodegenerative diseases, transplant rejections, and invasive angiogenesis.

Polynucleotides Encoding Anti-SEMA4D Antibodies

This disclosure also provides an isolated polynucleotide, or two or more polynucleotides comprising one or more nucleic acid sequences encoding an anti-SEMA4D binding molecule, e.g., an antibody or antigen-binding fragment, variant, or derivative thereof as provided herein.

In one aspect the disclosure provides an isolated polynucleotide or combination of polynucleotides comprising one or more nucleic acid sequences encoding an anti-SEMA4D binding molecule, e.g., antibody or fragment, variant, or derivative thereof as provided herein, or a subunit thereof, e.g., a heavy chain subunit or fragment thereof or a light chain subunit or fragment thereof In certain aspects, a polynucleotide or combination of polynucleotides as provided herein comprises a nucleic acid sequence that encodes the VH of the anti-SEMA4D binding molecule, e.g., antibody or fragment, variant, or derivative thereof. In certain aspects, a polynucleotide or combination of polynucleotides as provided herein comprises a nucleic acid sequence that encodes the VL of the anti-SEMA4D binding molecule, e.g., antibody or fragment, variant, or derivative thereof. In certain aspects, a polynucleotide or combination of polynucleotides as provided herein comprises a nucleic acid sequence that encodes the VH and a nucleic acid sequence that encodes the VL of the anti-SEMA4D binding molecule, e.g., antibody or fragment, variant, or derivative thereof. In certain aspects, the VH-encoding nucleic acid sequence and the VL-encoding nucleic acid sequence are situated on the same vector. Such a vector is provided by the disclosure. In certain aspects, the VH-encoding nucleic acid sequence and the VL-encoding nucleic acid sequence are situated on separate vectors. Such vectors are also provided by the disclosure. Vectors provided by the disclosure can further comprise genetic elements to allow expression of the antibody or fragment thereof. Such genetic elements, such as promoters, poly-adenylation sequences, and enhancers, are described elsewhere herein. The disclosure further provides a host cell comprising the polynucleotide or combination of polynucleotides provided herein, and/or the vector or vectors provided herein.

Also provided is a method for producing the anti-SEMA4D antibody or fragment, variant, or derivative thereof as provided herein, where the method comprises culturing a host cell as provided herein and recovering the antibody or fragment thereof In certain aspects the disclosure provides an isolated polynucleotide, or two or more polynucleotides comprising one or more nucleic acid sequences encoding an anti-SEMA4D antibody or antigen-binding fragment, variant, or derivative thereof, or a subunit thereof, where the antibody comprises a VH and a VL, the VH comprising complementarity determining regions (HCDRs) HCDR1, HCDR2, and HCDR3 comprising amino acid sequences identical or identical except for one, two, three, or four amino acid substitutions in one, two, or all three of the HCDRs to SEQ ID NO: 2, SEQ ID NO: 3, and SEQ ID NO: 4, respectively; and the VL comprising complementarity determining regions (LCDRs) LCDR1, LCDR2, and LCDR3 comprising amino acid sequences identical or identical except for one, two, three, or four amino acid substitutions in one, two, or all three of the LCDRs to SEQ ID NO: 6, SEQ ID NO: 7, and SEQ ID NO: 8, respectively.

In certain aspects the disclosure provides an isolated polynucleotide, or two or more polynucleotides comprising one or more nucleic acid sequences encoding an anti-SEMA4D antibody or antigen-binding fragment, variant, or derivative thereof, or a subunit thereof, where the antibody comprises a VH and a VL, The VH comprising an amino acid sequence at least 80%, 85%, 90%, 95%, 96%, 97%, 98%, 99% or 100% identical to SEQ ID NO: 1, and the VL comprising an amino acid sequence at least 80%, 85%, 90%, 95%, 96%, 97%, 98%, 99% or 100% identical to SEQ ID NO: 5.

Any of the polynucleotides described above can further include additional nucleic acid sequences, encoding, e.g., heavy or light chain constant regions or fragments thereof as described elsewhere herein, a signal peptide to direct secretion of the encoded polypeptide, or other heterologous polypeptides as described herein. Also, as described in more detail elsewhere herein, this disclosure includes compositions comprising one or more of the polynucleotides described above.

In one embodiment, this disclosure includes compositions comprising a first polynucleotide and second polynucleotide, the first polynucleotide comprising a nucleic acid sequence encoding a VH as described herein and the second polynucleotide encoding a VL as described herein.

This disclosure also includes fragments of the polynucleotides provided herein, as described elsewhere. Additionally, provided are polynucleotides that encode fusion polypeptides, Fab fragments, and other derivatives, as described herein.

Polynucleotides provided by this disclosure can be produced or manufactured by any method known in the art. For example, if the nucleotide sequence of the antibody is known, a polynucleotide encoding the antibody can be assembled from chemically synthesized oligonucleotides (e.g., as described in Kutmeier et al., Bio Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-SEMA4D binding molecule, e.g., an antibody, or antigen-binding fragment, variant, or derivative thereof as provided herein can be generated from nucleic acid sequences derived from a suitable source. If a clone containing a polynucleotide encoding a particular antibody is not available, but the sequence of the antibody molecule is known, a nucleic acid encoding the antibody can be chemically synthesized or obtained from a suitable source (e.g., an antibody cDNA library, or a cDNA library generated from, or nucleic acid, e.g., poly A+RNA, isolated from, any tissue or cells expressing the antibody or other anti-SEMA4D antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other anti-SEMA4D antibody. Amplified nucleic acids generated by PCR can then be cloned into replicable cloning vectors using any method well known in the art.

Once the nucleotide sequence and corresponding amino acid sequence of the anti-SEMA4D antibody, or antigen-binding fragment, variant, or derivative thereof is determined, its nucleotide sequence can be manipulated using methods well known in the art for the manipulation of nucleotide sequences, e.g., recombinant DNA techniques, site directed mutagenesis, PCR, etc. (see, for example, the techniques described in Sambrook et al. (1990) Molecular Cloning, A Laboratory Manual (2nd ed.; Cold Spring Harbor Laboratory, Cold Spring Harbor, N.Y.) and Ausubel et al., eds. (1998) Current Protocols in Molecular Biology (John Wiley & Sons, NY), which are both incorporated by reference herein in their entireties), to generate antibodies having a different amino acid sequence, for example to create amino acid substitutions, deletions, and/or insertions.

A polynucleotide or combination of polynucleotides encoding an anti-SEMA4D binding molecule, e.g., an antibody, or antigen-binding fragment, variant, or derivative thereof, can be composed of any polyribonucleotide or polydeoxyribonucleotide, which can be unmodified RNA or DNA, or modified RNA or DNA. For example, a polynucleotide or combination of polynucleotides encoding an anti-SEMA4D antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, a polynucleotide or combination of polynucleotides encoding an anti-SEMA4D binding molecule, e.g., an antibody, or antigen-binding fragment, variant, or derivative thereof can be composed of triple-stranded regions comprising RNA or DNA or both RNA and DNA.

A polynucleotide or combination of polynucleotides encoding an anti-SEMA4D binding molecule, e.g., antibody, or antigen-binding fragment, variant, or derivative thereof, can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide or combination of polynucleotides encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations can be introduced by standard techniques, such as site-directed mutagenesis and PCR-mediated mutagenesis. In certain aspects, conservative amino acid substitutions can be made at one or more non-essential amino acid residues.

Fusion Proteins and Antibody Conjugates

As discussed in more detail elsewhere herein, an anti-SEMA4D binding molecule, e.g., an antibody or antigen-binding fragment, variant, or derivative thereof as provided herein, can further be recombinantly fused to a heterologous polypeptide at the N- or C-terminus or chemically conjugated (including covalent and non-covalent conjugations) to polypeptides or other heterologous moieties. For example, anti-SEMA4D antibodies can be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No.

5,314,995; and EP 396,387. In certain aspects, the heterologous moiety can be a polypeptide, a cytotoxic agent, a therapeutic agent, a prodrug, a lipid, a carbohydrate, a nucleic acid, a detectable label, a polymer, or any combination thereof. Exemplary heterologous polypeptides include, without limitation, a binding molecule, an enzyme, a cytokine, a lymphokine, a hormonal peptide, or any combination thereof. Exemplary cytotoxic agents include, without limitation a radionuclide, a biological toxin, an enzymatically active toxin, or any combination thereof. Exemplary detectable labels include, without limitation, an enzyme, a fluorescent label, a chemiluminescent label, a bioluminescent label, a radioactive label, or any combination thereof An anti-SEMA4D binding molecule, e.g., an antibody or antigen-binding fragment, variant, or derivative thereof as provided herein can include derivatives that are modified, e.g., by the covalent attachment of any type of moiety to the antibody such that covalent attachment does not prevent the binding molecule from binding to SEMA4D. For example, but not by way of limitation, an antibody derivative can be modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

An anti-SEMA4D binding molecule, e.g., an antibody or antigen-binding fragment, variant, or derivative thereof as provided herein can be composed of amino acids joined to each other by peptide bonds or modified peptide bonds, e.g., peptide isosteres, and can contain amino acids other than the 20 gene-encoded amino acids. For example, an anti-SEMA4D binding molecule, e.g., an antibody or antigen-binding fragment, variant, or derivative thereof as provided herein can be modified by natural processes, such as post-translational processing, or by chemical modification techniques that are well known in the art. Such modifications are well described in basic texts and in more detailed monographs, as well as in a voluminous research literature. Modifications can occur anywhere in the anti-SEMA4D binding molecule, including the peptide backbone, the amino acid side-chains and the amino or carboxyl termini, or on moieties such as carbohydrates. Also, a given anti-SEMA4D binding molecule can contain many types of modifications. Anti-SEMA4D binding molecules can be branched, for example, as a result of ubiquitination, and they can be cyclic, with or without branching. Cyclic, branched, and branched cyclic anti-SEMA4D binding molecule can result from posttranslational natural processes or can be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, T. E. Creighton, W. H. Freeman and Company, NY; 2nd ed. (1993); Johnson, ed. (1983) Post-translational Covalent Modification of Proteins (Academic Press, NY), pgs. 1-12; Seifter et al., Meth. Enzymol. 182: 626-646 (1990); Rattan et al., Ann. NY Acad. Sci. 663:48-62 (1992)).

This disclosure also provides for fusion proteins comprising an anti-SEMA4D binding molecule, e.g., an antibody or antigen-binding fragment, variant, or derivative thereof as provided herein, and a heterologous polypeptide. The heterologous polypeptide to which the antibody is fused can be useful for function or is useful to target the anti-SEMA4D polypeptide expressing cells. An anti-SEMA4D binding molecule, e.g., an antibody or antigen-binding fragment, variant, or derivative thereof as provided herein can be fused or conjugated to one or more heterologous polypeptides or other moieties to increase the in vivo half-life of the polypeptides or for use in immunoassays using methods known in the art. For example, in one embodiment, PEG or human serum albumin can be fused or conjugated to an anti-SEMA4D binding molecule as provided herein to increase their half-life in vivo. See Leong et al., Cytokine 16:106 (2001); Adv. in Drug Deliv. Rev. 54:531 (2002); or Weir et al., Biochem. Soc. Transactions 30:512 (2002).

Moreover, an anti-SEMA4D binding molecule, e.g., an antibody or antigen-binding fragment, variant, or derivative thereof as provided herein can be fused to one or more marker sequences, such as a peptide to facilitate their purification or detection. In certain embodiments, the marker amino acid sequence is a hexa-histidine peptide, such as the tag provided in a pQE vector (QIAGEN, Inc.), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

Fusion proteins can be prepared using methods that are well known in the art (see for example U.S. Pat. Nos. 5,116,964 and 5,225,538). The precise site at which the fusion is made can be selected empirically to optimize the secretion or binding characteristics of the fusion protein. DNA encoding the fusion protein is then transfected into a host cell for expression.

An anti-SEMA4D binding molecule, e.g., an antibody or antigen-binding fragment, variant, or derivative thereof as provided herein can be used in non-conjugated form or can be conjugated to at least one of a variety of molecules, e.g., to improve the therapeutic properties of the molecule, to facilitate target detection, or for imaging or therapy of the patient. An anti-SEMA4D binding molecule, e.g., an antibody or antigen-binding ragment, variant, or derivative thereof as provided herein can be labeled or conjugated either before or after purification, or when purification is performed.

In particular, an anti-SEMA4D binding molecule, e.g., an antibody or antigen-binding fragment, variant, or derivative thereof as provided herein can be conjugated to therapeutic agents, prodrugs, cytotoxic agents, peptides, proteins, enzymes, viruses, lipids, biological response modifiers, pharmaceutical agents, or PEG.

Those skilled in the art will appreciate that conjugates can also be assembled using a variety of techniques depending on the selected agent to be conjugated. For example, conjugates with biotin are prepared, e.g., by reacting a binding polypeptide with an activated ester of biotin such as the biotin N-hydroxysuccinimide ester. Similarly, conjugates with a fluorescent marker can be prepared in the presence of a coupling agent, e.g., those listed herein, or by reaction with an isothiocyanate, e.g., fluorescein-isothiocyanate. Conjugates of an anti-SEMA4D binding molecule, e.g., an antibody or antigen-binding fragment, variant, or derivative thereof as provided herein can be prepared in an analogous manner.

This disclosure further encompasses an anti-SEMA4D binding molecule, e.g., an antibody or antigen-binding fragment, variant, or derivative thereof as provided herein conjugated to a diagnostic or therapeutic agent. Such anti-SEMA4D binding molecules can be used diagnostically to, for example, monitor the development or progression of a disease as part of a clinical testing procedure to, e.g., determine the efficacy of a given treatment and/or prevention regimen. For example, detection can be facilitated by coupling the anti-SEMA4D binding molecule to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to this disclosure. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In, $^{90}$Y, or $^{99}$Tc.

An anti-SEMA4D binding molecule, e.g., an antibody, or antigen-binding fragment, variant, or derivative thereof as provided herein, can be conjugated to a therapeutic moiety such as a cytotoxin, a therapeutic agent or a radioactive metal ion. A cytotoxin or cytotoxic agent includes any agent that is detrimental to cells.

An anti-SEMA4D binding molecule, e.g., an antibody, or antigen-binding fragment, variant, or derivative thereof as provided herein, can also be detectably labeled by coupling it to a chemiluminescent compound. The presence of the chemiluminescent-tagged anti-SEMA4D binding molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an anti-SEMA4D binding molecule, e.g., an antibody or antigen-binding fragment, variant, or derivative thereof as provided herein can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md.; Diagnostic Horizons 2:1-7 (1978); Voller et al., J. Clin. Pathol. 31:507-520 (1978); Butler, Meth. Enzymol. 73:482-523 (1981); Maggio, ed. (1980) Enzyme Immunoassay, CRC Press, Boca Raton, Fla.; Ishikawa et al., eds. (1981) Enzyme Immunoassay (Kgaku Shoin, Tokyo). The enzyme, which is bound to the anti-SEMA4D binding molecule will react with an appropriate substrate, e.g., a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, those phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the anti-SEMA4D binding molecule, it is possible to detect the binding molecule through the use of a radioimmunoassay (MA). The radioactive isotope can be detected by means including, but not limited to, a gamma counter, a scintillation counter, or autoradiography.

An anti-SEMA4D binding molecule, e.g., antibody, or antigen-binding fragment, variant, or derivative thereof as provided herein, can also be detectably labeled using fluorescence emitting metals such as $^{152}$Eu, or others of the lanthanide series. These metals can be attached to the binding molecule using such metal chelating groups as diethylenetriaminepentacetic acid (DTPA) or ethylenediaminetetraacetic acid (EDTA).

Techniques for conjugating various moieties to an anti-SEMA4D binding molecule as provided herein are well known by those of ordinary skill in the art.

Expression of Antibody Polypeptides

DNA sequences that encode the light and the heavy chains of an anti-SEMA4D binding molecule, e.g., an antibody or antigen-binding fragment, variant, or derivative thereof as provided herein can be made, either simultaneously or separately, using reverse transcriptase and DNA polymerase in accordance with well-known methods. PCR can be initiated by consensus constant region primers or by more specific primers based on the published heavy and light chain DNA and amino acid sequences. As discussed above, PCR also can be used to isolate DNA clones encoding the antibody light and heavy chains. In this case the libraries can be screened by consensus primers or larger homologous probes, such as mouse constant region probes.

DNA, typically plasmid DNA, can be isolated from the cells using techniques known in the art, restriction mapped and sequenced in accordance with standard, well known techniques set forth in detail, e.g., in the references relating to recombinant DNA techniques provided elsewhere herein.

Following manipulation of the isolated genetic material to provide an anti-SEMA4D binding molecule, e.g., an antibody or antigen-binding fragment, variant, or derivative thereof as provided herein, the polynucleotides encoding the binding molecule can be inserted into an expression vector for introduction into one or more host cells that can be used to produce the desired quantity of anti-SEMA4D binding molecule.

Recombinant expression of an anti-SEMA4D antibody, or fragment, derivative or analog thereof, e.g., a heavy or light chain of an antibody, requires construction of one or more expression vectors containing a polynucleotide or combination of polynucleotides that encodes the antibody. Once a polynucleotide or combination of polynucleotides encoding the antibody molecule or a heavy or light chain of an antibody, or portion thereof (e.g., containing the heavy or light chain variable region) has been obtained, the vector or vectors for the production of the antibody molecule can be produced by recombinant DNA technology using techniques well known in the art. Thus, methods for preparing a protein by expressing a polynucleotide or combination of polynucleotides containing the antibody-encoding nucleic acid sequences are described herein. Methods that are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. This disclosure, thus, provides replicable vectors comprising nucleic acid sequences encoding an anti-SEMA4D binding molecule, e.g., an antibody as provided herein or a heavy or light chain thereof, or a heavy or light chain variable region, operably linked to a promoter. Such vectors can include the nucleotide sequence encoding a constant region of the antibody heavy and/or light chain (see, e.g., PCT Publication WO 86/05807; PCT Publication WO 89/01036; and U.S. Pat. No. 5,122,464) and the variable region of the antibody can be cloned into such a vector for expression of the entire heavy or light chain The term "vector" or "expression vector" is used herein to mean vectors used in accordance with this disclosure as a vehicle for introducing into and expressing a desired gene in a host cell. As known to those skilled in the art, such vectors can easily be selected from among, e.g., plasmids, phages, and viruses, e.g., retroviruses. In general, vectors compatible with this disclosure will comprise a selection marker, appropriate restriction sites to facilitate cloning of the desired gene and the ability to enter and/or replicate in eukaryotic or prokaryotic cells.

Numerous expression vector systems can be employed. For example, one class of vector utilizes DNA elements that are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites (IRES). Additionally, cells that have integrated the DNA into their chromosomes can be selected by introducing one or more markers which allow for the selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed or introduced into the same cell by cotransformation. Additional elements can also be needed for optimal synthesis of mRNA. These elements can include signal sequences, splice signals, as well as transcriptional promoters, enhancers, and termination signals.

In certain aspects the cloned variable region nucleic acid molecules can be inserted into an expression vector along with the heavy and light chain constant region genes synthesized as discussed above. Of course, any expression vector that is capable of eliciting expression in eukaryotic cells can be used. Examples of suitable vectors include, but are not limited to plasmids pcDNA3, pHCMV/Zeo, pCR3.1, pEF 1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those that express suitably high levels if immunoglobulin heavy and light chains is routine experimentation that can be carried out, for example, by robotic systems.

More generally, once the vector or DNA sequence encoding a monomeric subunit of an anti-SEMA4D binding molecule, e.g., an antibody or antigen-binding fragment, variant, or derivative thereof as provided herein has been prepared, the expression vector can be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway (1988) "Mammalian Expression Vectors" in Vectors, ed. Rodriguez and Denhardt (Butterworths, Boston, Mass.), Chapter 24.2, pp. 470-472. Typically, plasmid introduction into the host is via electroporation. The host cells harboring the expression construct can be grown under conditions appropriate to the production of the light chains and heavy chains and assayed for heavy and/or light chain protein synthesis and assembly. Exemplary assay techniques include enzyme-linked immunosorbent assay (ELISA), radioimmunoassay (MA), or fluorescence-activated cell sorter analysis (FACS), immunohistochemistry and the like.

An expression vector can be transferred to a host cell by conventional techniques, and the transfected cells can then be cultured by conventional techniques to produce an anti-SEMA4D binding molecule, e.g., an antibody or antigen-binding fragment, variant, or derivative thereof as provided herein. Thus, this disclosure includes host cells containing a polynucleotide or combination of polynucleotides encoding an antibody as provided herein, or a heavy or light chain thereof, operably linked to a promoter, e.g., a heterologous promoter. In certain embodiments for the expression of double-chained antibodies, vectors encoding both the heavy and light chains can be co-expressed in the host cell for expression and assembly of the entire binding molecule, as detailed below.

As used herein, "host cells" refers to cells that harbor vectors constructed using recombinant DNA techniques and encoding at least one heterologous polynucleotide. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" can mean either from spun down whole cells, or from the cell culture containing both the medium and the suspended cells.

A variety of host-expression vector systems can be utilized to express an anti-SEMA4D binding molecule, e.g., an antibody or antigen-binding fragment, variant, or derivative thereof as provided herein. Such host-expression systems represent vehicles by which the coding sequences of interest can be produced and subsequently purified, but also represent cells that can, when transformed or transfected with the appropriate nucleotide coding sequences, express an antibody molecule as provided herein in situ. These include, but are not limited to, microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter, or the human cytomegalovirus immediate early promoter). In certain aspects, bacterial cells such as *Escherichia colt*, or eukaryotic cells, especially for the expression of whole recombinant antibody molecules, can be used for the expression of a recombinant antibody molecule. For example, mammalian cells such as Chinese hamster ovary cells (CHO), in conjunction with a vector are an effective expression system for antibodies (Foecking et al., Gene 45:101 (1986); Cockett et al., Bio/Technology 8:2 (1990)).

The host cell line used for protein expression can be of mammalian origin. Exemplary host cell lines include, but are not limited to, CHO (Chinese Hamster Ovary), DG44 and DUXB11 (Chinese Hamster Ovary lines, DHFR minus), HeLa (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3.times.63-Ag3 0.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain can be chosen that modulates the expression of the inserted sequences or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used.

For long-term, high-yield production of recombinant proteins, stable expression can be used. For example, cell lines that stably express the antibody molecule can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which stably express the antibody molecule.

The expression levels of an antibody molecule can be increased by vector amplification (for a review, see Bebbington and Hentschel (1987) "The Use of Vectors Based on Gene Amplification for the Expression of Cloned Genes in Mammalian Cells in DNA Cloning" (Academic Press, N.Y.) Vol. 3. When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

In vitro production allows scale-up to give large amounts of the desired polypeptides. Techniques for mammalian cell cultivation under tissue culture conditions are known in the art and include homogeneous suspension culture, e.g., in an airlift reactor or in a continuous stirrer reactor, or immobilized or entrapped cell culture, e.g., in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-) affinity chromatography, e.g., after biosynthesis of a synthetic hinge region polypeptide or prior to or subsequent to the HIC chromatography step described herein.

Nucleic acid molecules encoding an anti-SEMA4D binding molecule, e.g., an antibody or antigen-binding fragment, variant, or derivative thereof as provided herein can also be expressed in non-mammalian cells such as insect, bacteria or yeast or plant cells. Bacteria that readily take up nucleic acids include members of the enterobacteriaceae, such as strains of *Escherichia coli* or *Salmonella*; and bacillaceae, such as *Bacillus subtilis*; Pneumococcus; *Streptococcus*, and *Haemophilus influenzae*. It will further be appreciated that, when expressed in bacteria, the heterologous polypeptides typically become part of inclusion bodies. Inclusion bodies can be isolated, purified and then assembled into functional molecules. Where tetravalent forms of antibodies are desired, the subunits can then self-assemble into tetravalent antibodies (WO 02/096948A2).

In bacterial systems, a number of expression vectors can be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified can be desirable.

In addition to prokaryotes, eukaryotic microbes can also be used. *Saccharomyces cerevisiae*, or common baker's yeast, is the most commonly used among eukaryotic microorganisms although a number of other strains are commonly available, e.g., *Pichia pastoris*.

In an insect system, *Autographa californica* nuclear polyhedrosis virus (AcNPV) is typically used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

Once an anti-SEMA4D binding molecule, e.g., an antibody or antigen-binding fragment, variant, or derivative thereof as provided herein has been recombinantly expressed, it can be purified by any method known in the art for purification of an immunoglobulin molecule, for example, by chromatography (e.g., ion exchange, affinity, particularly by affinity for Protein A, and sizing column chromatography), centrifugation, differential solubility, or by any other standard technique for the purification of proteins. Alternatively, methods for increasing the affinity of antibodies as provided herein is disclosed in U.S. Patent Application Publication No. 2002 0123057 A1.

Treatment Methods Using Therapeutic
Anti-SEMA4D Antibodies

This disclosure provides methods for the use of an anti-SEMA4D binding molecule, e.g., an antibody or antigen-binding fragment, variant, or derivative thereof as provided herein, to treat subjects having a disease or disorder associated with SEMA4D pathology.

The following discussion refers to diagnostic methods and treatment of various diseases and disorders with an anti-SEMA4D binding molecule, e.g., an antibody or antigen-binding fragment, variant, or derivative thereof as provided herein, e.g., capable of specifically binding SEMA4D, e.g., human, mouse, or human and mouse SEMA4D, and having SEMA4D neutralizing activity.

In one aspect, the disclosure provides a method for neutralizing SEMA4D in a human subject, comprising administering to the human subject an anti-SEMA4D binding molecule, e.g., an antibody or antigen-binding fragment, variant, or derivative thereof as provided herein. In certain aspects, the human subject is in need of treatment for an autoimmune disease or disorder, an inflammatory disease or disorder, cancer, a neuroinflammatory disease or disorder, a neurodegenerative disease or disorder, or any combination thereof. In certain aspects, the neuroinflammatory disease or disorder is multiple sclerosis. In certain aspects, the neurodegenerative disease or disorder is stroke, Alzheimer's disease, Parkinson's disease, Huntington's disease, Down syndrome, ataxia, amyotrophic lateral sclerosis (ALS), frontotemporal dementia (FTD), HIV-related cognitive impairment, CNS Lupus, mild cognitive impairment, or a combination thereof. In certain aspects, the autoimmune disease or the inflammatory disease is arthritis, e.g., rheumatoid arthritis, atherosclerosis (see e.g., PCT Publication No. WO 2015/054628, which is incorporated herein by reference in its entirety), or osteodegenerative diseases such as osteoporosis (see, e.g., U.S. Pat. No. 9,447,191, which is incorporated herein by reference in its entirety).

In one aspect, treatment includes the application or administration of an anti-SEMA4D binding molecule, e.g., an antibody or antigen-binding fragment, variant, or derivative thereof as provided herein to a subject, or application or administration to an isolated tissue or cell line from a subject, where the subject has a disease, a symptom of a disease, or a predisposition toward a disease. In another aspect, treatment also includes the application or administration of a pharmaceutical composition comprising an anti-SEMA4D binding molecule, e.g., an antibody or antigen-binding fragment, variant, or derivative thereof as provided herein to a subject, or to an isolated tissue or cell line from a patient, who has a disease, a symptom of a disease, or a predisposition toward a disease.

In one aspect, an anti-SEMA4D binding molecule, e.g., an antibody or antigen-binding fragment, variant, or derivative thereof as provided herein can be useful for the treatment cancer, e.g., treatment of various malignant and non-malignant tumors. By "anti-tumor activity" is intended a reduction in the rate of malignant cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. For example, therapy with an anti-SEMA4D binding molecule, e.g., an antibody or antigen-binding fragment, variant, or derivative thereof as provided herein can elicit a physiological response, for example, a reduction in angiogenesis or migration of CTL to the tumor microenvironment. Methods for treating cancer with an anti-SEMA4D binding molecule, e.g., an antibody or antigen-binding fragment, variant, or derivative thereof as provided herein can be found, e.g., in PCT Publication No. WO 2014/209802 [combo immunotherapy], which is incorporated herein by reference in its entirety.

In one aspect, the disclosure provides an anti-SEMA4D binding molecule, e.g., an antibody or antigen-binding fragment, variant, or derivative thereof as provided herein for use as a medicament, in particular for use in the treatment or prophylaxis of cancer or for use in a precancerous condition or lesion.

In another aspect, an anti-SEMA4D binding molecule, e.g., an antibody or antigen-binding fragment, variant, or derivative thereof as provided herein can be useful for treatment of an autoimmune disease or inflammatory disease. In another aspect, an anti-SEMA4D binding molecule, e.g., an antibody or antigen-binding fragment, variant, or derivative thereof as provided herein can be useful for treatment of a neuroinflammatory or neurodegenerative disease. Methods for treating neuroinflammatory or neurodegenerative diseases can be found, e.g., in PCT Publication No. WO 2013/055922 [BBB], PCT Publication No. WO 2015/061330 [HD], and PCT Publication No. WO 2013/170221 [neurogenesis/stroke], the contents of which are incorporated by reference herein in their entireties.

In accordance with the methods provided herein, an anti-SEMA4D binding molecule, e.g., an antibody or antigen-binding fragment, variant, or derivative thereof as provided herein can be used to promote a positive therapeutic response with respect to a malignant human cell. By "positive therapeutic response" with respect to cancer treatment is intended an improvement in the disease in association with the anti-tumor activity of these binding molecules, e.g., antibodies or fragments thereof, and/or an improvement in the symptoms associated with the disease. That is, an anti-proliferative effect, the prevention of further tumor outgrowths, a reduction in tumor size, a decrease in tumor vasculature, a reduction in the number of cancer cells, and/or a decrease in one or more symptoms associated with the disease can be observed. Thus, for example, an improvement in the disease can be characterized as a complete response. By "complete response" is intended an absence of clinically detectable disease with normalization of any previously abnormal radiographic studies, bone marrow, and cerebrospinal fluid (CSF). Alternatively, an improvement in the disease can be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only.

An anti-SEMA4D binding molecule, e.g., an antibody or antigen-binding fragment, variant, or derivative thereof as provided herein can also find use in the treatment of inflammatory diseases and deficiencies or disorders of the immune system. Inflammatory diseases are characterized by inflammation and tissue destruction, or a combination thereof. By "anti-inflammatory activity" is intended a reduction or prevention of inflammation. "Inflammatory disease" includes any inflammatory immune-mediated process where the initiating event or target of the immune response involves non-self-antigen(s), including, for example, alloantigens, xenoantigens, viral antigens, bacterial antigens, unknown antigens, or allergens. In one embodiment, the inflammatory disease is an inflammatory disorder of the peripheral or central nervous system. In another embodiment, the inflammatory disease is an inflammatory disorder of the joints.

Further, the term "inflammatory disease(s)" includes "autoimmune disease(s)." As used herein, the term "autoimmunity" is generally understood to encompass inflammatory immune-mediated processes involving "self" antigens. In autoimmune diseases, self-antigen(s) trigger host immune responses. An autoimmune disease can result from an inappropriate immune response directed against a self-antigen (an autoantigen), which is a deviation from the normal state of self-tolerance. In general, antibodies (particularly, but not exclusively, IgG antibodies), acting as cytotoxic molecules or as immune complexes, are the principal mediators of various autoimmune diseases, many of which can be debilitating or life-threatening.

In one embodiment, an anti-SEMA4D binding molecule, e.g., an antibody or antigen-binding fragment, variant, or derivative thereof as provided herein can be used to treat multiple sclerosis (MS). MS, also known as disseminated sclerosis or encephalomyelitis disseminata, is an autoimmune condition in which the immune system attacks the central nervous system, leading to demyelination. The name multiple sclerosis refers to the scars (scleroses, also referred to as plaques or lesions) that form in the nervous system. MS lesions commonly involve white matter areas close to the ventricles of the cerebellum, brain stem, basal ganglia and spinal cord, and the optic nerve. MS results in destruction of oligodendrocytes, the cells responsible for creating and maintaining the myelin sheath. MS results in a thinning or complete loss of myelin and, as the disease advances, transection of axons.

Neurological symptoms can vary with MS, and the disease often progresses to physical and cognitive disability. MS takes several forms, with new symptoms occurring either in discrete attacks (relapsing forms) or slowly accumulating over time (progressive forms). Between attacks, symptoms can go away completely, but permanent neurological damage often results, especially as the disease advances.

Neutralization of SEMA4D using an anti-SEMA4D binding molecule, e.g., an antibody or antigen-binding fragment, variant, or derivative thereof as provided herein can be used to reduce the severity of MS through several different mechanisms, e.g., anti-SEMA4D monoclonal antibodies can block immune maturation and activation by SEMA4D to reduce the rate of relapse by reducing secondary immune responses to CNS antigens, and anti-SEMA4D monoclonal antibodies can block the effect of soluble SEMA4D in mediating apoptosis of oligodendrocytes in the CNS can reduce disease severity by reducing demyelination.

In one aspect, an anti-SEMA4D binding molecule, e.g., an antibody or antigen-binding fragment, variant, or derivative thereof as provided herein can be used to treat arthritis. Arthritis, is an inflammatory disease of the joints, which can be caused by an autoimmune condition in which the immune system attacks the joints. In certain embodiments, the arthritis is selected from the group consisting of osteoarthritis, gouty arthritis, ankylosing spondylitis, psoriatic arthritis, reactive arthritis, rheumatoid arthritis, juvenile onset rheumatoid arthritis, infectious arthritis, inflammatory arthritis, septic arthritis, degenerative arthritis, arthritis mutilans, and Lyme arthritis. In one embodiment, the arthritis is rheumatoid arthritis (RA).

This disclosure includes methods of treating or preventing arthritis by administering to a subject an anti-SEMA4D binding molecule as provided herein. Methods as provided herein can reduce the pain, swelling, or stiffness associated with arthritis, e.g., rheumatoid arthritis. This disclosure is also directed to methods for improving joint performance, function, and health. In some embodiments of this disclosure, treatment results in a decrease in arthritis severity scores, a decrease in arthritis severity/area under curve, a decrease in histopathology parameters associated with arthritis (inflammation, pannus, cartilage damage, and bone damage), a decrease in serum arachidonic acid levels, or a decrease in anti-collagen antibodies. In certain embodiments, beneficial or desired clinical results include, but are not limited to, alleviation of symptoms associated with arthritis; prevention of arthritis; delay in the onset of arthritis; reduced incidence of arthritis in a population; diminishment of the extent of the condition associated with arthritis; stabilization (e.g., not worsening) of the state of the condition, disorder or disease associated with arthritis; delay in onset or slowing of the condition, disorder or disease progression associated with arthritis; amelioration of the condition, disorder or disease state, remission (whether partial or total) of the condition, disorder or disease associated with arthritis, whether detectable or undetectable; or enhancement or improvement of the condition, disorder or disease associated with arthritis.

The methods provided herein can be used to treat individuals who have arthritis or individuals who are at risk for developing arthritis. Thus, in some embodiments this disclosure provides a method of treating a subject having normal joints, borderline arthritic joints, or very arthritic joints, the method comprising administering an anti-SEMA4D binding molecule as provided herein to a subject as described herein. In some embodiments, the methods provided herein can be used to treat chronic arthritis for the remainder of the life of the subject.

In accordance with the methods of as provided herein, an anti-SEMA4D binding molecule, e.g., an antibody or antigen-binding fragment, variant, or derivative thereof as provided herein can be used to promote a positive therapeutic response with respect to treatment or prevention of an autoimmune disease and/or inflammatory disease. By "positive therapeutic response" with respect to an autoimmune disease and/or inflammatory disease is intended an improvement in the disease in association with the anti-inflammatory activity, anti-angiogenic activity, anti-apoptotic activity, or the like, of these antibodies, and/or an improvement in the symptoms associated with the disease. That is, an anti-proliferative effect, the prevention of further proliferation of SEMA4D-expressing cells, a reduction in the inflammatory response including but not limited to reduced secretion of inflammatory cytokines, adhesion molecules, proteases, immunoglobulins (in instances where the SEMA4D bearing cell is a B cell), combinations thereof, and the like, increased production of anti-inflammatory proteins, a reduction in the number of autoreactive cells, an increase in immune tolerance, inhibition of autoreactive cell survival, reduction in apoptosis, reduction in endothelial cell migration, increase in spontaneous monocyte migration, reduction in and/or a decrease in one or more symptoms mediated by stimulation of sSEMA4D or SEMA4D-expressing cells can be observed. Such positive therapeutic responses are not limited to the route of administration and can comprise administration to the donor, the donor tissue (such as for example organ perfusion), the host, any combination thereof, and the like.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with an anti-SEMA4D binding molecule, e.g., an antibody or antigen-binding fragment, variant, or derivative thereof as provided herein can experience the beneficial effect of an improvement in the symptoms associated with the disease.

An anti-SEMA4D binding molecule, e.g., an antibody or antigen-binding fragment, variant, or derivative thereof as provided herein can be used in combination with at least one other cancer therapy, including, but not limited to, surgery or surgical procedures; immune modulating therapy, radiation therapy; chemotherapy, optionally in combination with autologous bone marrow transplant, or other cancer therapy; where the additional cancer therapy is administered prior to, during, or subsequent to the anti-SEMA4D binding molecule, e.g., antibody or antigen binding fragment thereof, therapy. Thus, where the combined therapies comprise administration of an anti-SEMA4D binding molecule, e.g., an antibody or antigen binding fragment thereof as provided herein in combination with administration of another therapeutic agent, as with chemotherapy, radiation therapy, other anti-cancer antibody therapy, small molecule-based cancer therapy, or vaccine/immunotherapy-based cancer therapy, the methods as provided herein encompass coadministration, using separate formulations or a single pharmaceutical formulation, or and consecutive administration in either order.

An anti-SEMA4D binding molecule, e.g., an antibody or antigen-binding fragment, variant, or derivative thereof as provided herein can be used in combination with any known therapies for autoimmune and inflammatory diseases, including any agent or combination of agents that are known to be useful, or which have been used or are currently in use, for treatment of autoimmune and inflammatory diseases. Thus, where the combined therapies comprise administration of an anti-SEMA4D binding molecule in combination with administration of another therapeutic agent, the methods provided herein encompass coadministration, using separate formulations or a single pharmaceutical formulation, and consecutive administration in either order. In some embodiments, the anti-SEMA4D antibodies described herein are administered in combination with immunosuppressive drugs or anti-inflammatory drugs, wherein the antibody and the therapeutic agent(s) can be administered sequentially, in either order, or simultaneously (i.e., concurrently or within the same time frame).

In certain aspects, an anti-SEMA4D binding molecule, e.g., an antibody or antigen-binding fragment, variant, or derivative thereof as provided herein can be used alone or in combination with immunosuppressive drugs to treat and/or prevent rheumatoid arthritis. As discussed above, treatment effectiveness can be assessed using any means and includes, but is not limited to, effectiveness as measured by clinical responses defined by the American College of Rheumatology criteria, the European League of Rheumatism criteria, or any other criteria. See for example, Felson et al., Arthritis. Rheum. 38:727-35 (1995) and van Gestel et al., Arthritis Rheum. 39:34-40 (1996).

In yet other aspects, an anti-SEMA4D binding molecule, e.g., an antibody or antigen-binding fragment, variant, or derivative thereof as provided herein can be used alone or in combination with immunosuppressive drugs to treat and/or prevent multiple sclerosis.

A further aspect of this disclosure is the use of an anti-SEMA4D binding molecule, e.g., an antibody or antigen-binding fragment, variant, or derivative thereof as provided herein, for diagnostic monitoring of protein levels in tissue as part of a clinical testing procedure, e.g., to determine the efficacy of a given treatment regimen. For example, detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, $^{3}$H.

VIII. Pharmaceutical Compositions and Administration Methods

Methods of preparing and administering an anti-SEMA4D binding molecule, e.g., an antibody or antigen-binding fragment, variant, or derivative thereof as provided herein to a subject in need thereof are well known to or are readily determined by those skilled in the art. The route of administration of the anti-SEMA4D binding molecule can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are contemplated as being within the scope of this disclosure, an example of a form for administration would be a solution for injection, in particular for intravenous or intraarterial injection or drip. Usually, a suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, an anti-SEMA4D binding molecule, e.g., an antibody or antigen-binding fragment, variant, or derivative thereof as provided herein can be delivered directly to the site of the adverse condition, e.g., a solid tumor, thereby increasing the exposure of the diseased tissue to the therapeutic agent.

An anti-SEMA4D binding molecule, e.g., an antibody or antigen-binding fragment, variant, or derivative thereof as provided herein can be administered in a pharmaceutically effective amount for the in vivo treatment of SEMA4D-mediated diseases such as cancers, autoimmune diseases, inflammatory diseases including central nervous system (CNS) and peripheral nervous system (PNS) inflammatory diseases, neurodegenerative diseases, and invasive angiogenesis. In this regard, it will be appreciated that the disclosed binding molecules can be formulated so as to facilitate administration and promote stability of the active agent. In certain aspects, pharmaceutical compositions as provided herein can include a pharmaceutically acceptable, non-toxic, sterile carrier such as physiological saline, non-toxic buffers, preservatives and the like. For the purposes of the instant application, a pharmaceutically effective amount of an anti-SEMA4D binding molecule, e.g., an antibody or antigen-binding fragment, variant, or derivative thereof as provided herein, conjugated or unconjugated, means an amount sufficient to achieve effective binding to a target and to achieve a benefit, e.g., to ameliorate symptoms of a disease or disorder or to detect a substance or a cell.

The pharmaceutical compositions used in this disclosure comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration include, without limitation, sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. Pharmaceutically acceptable carriers include, but are not limited to, 0.01-0.1 M, e.g., 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as, for example, antimicrobials, antioxidants, chelating agents, and inert gases and the like.

In certain aspects, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and can be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In certain aspects isotonic agents, for example, sugars, polyalcohols, such as mannitol, sorbitol, or sodium chloride can be included in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-SEMA4D binding molecule, e.g., an antibody or antigen-binding fragment, variant, or derivative thereof as provided herein by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, methods of preparation can include vacuum drying and freeze-drying, which yields a powder of an active ingredient plus any additional desired ingredient from a previously sterile-filtered solution thereof The preparations for injections are processed, filled into containers such as ampoules, bags, bottles, syringes or vials, and sealed under aseptic conditions according to methods known in the art. Further, the preparations can be packaged and sold in the form of a kit such as those described in U.S. patent application Ser. No. 09/259,337. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions provided by this disclosure can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an anti-SEMA4D binding molecule, e.g., an antibody or antigen-binding fragment, variant, or derivative thereof as provided herein, that can be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

An anti-SEMA4D binding molecule, e.g., an antibody or antigen-binding fragment, variant, or derivative thereof as provided herein can be administered to a human or other animal in accordance with the aforementioned methods of treatment in an amount sufficient to produce a therapeutic effect. An anti-SEMA4D binding molecule, e.g., an antibody or antigen-binding fragment, variant, or derivative thereof as provided herein can be administered to a human or other animal in a conventional dosage form prepared by combining the antibody with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

By "therapeutically effective dose or amount" or "effective amount" is intended an amount of an anti-SEMA4D binding molecule, e.g., an antibody or antigen-binding fragment, variant, or derivative thereof as provided herein, that when administered brings about a positive therapeutic response with respect to treatment of a patient with a disease to be treated.

Therapeutically effective doses of a compositions as provided herein for treatment of SEMA4D-mediated diseases such as cancer; autoimmune diseases, e.g., arthritis, multiple sclerosis, inflammatory diseases including central nervous system (CNS) and peripheral nervous system (PNS) inflammatory diseases; neurodegenerative diseases; and invasive angiogenesis, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages can be titrated using routine methods known to those of skill in the art to optimize safety and efficacy.

The amount of an anti-SEMA4D binding molecule, e.g., an antibody or antigen-binding fragment, variant, or derivative thereof as provided herein to be administered is readily determined by one of ordinary skill in the art without undue experimentation. Factors influencing the mode of administration and the respective amount of anti-SEMA4D binding molecule include, but are not limited to, the severity of the disease, the history of the disease, and the age, height, weight, health, and physical condition of the individual undergoing therapy. Similarly, the amount of anti-SEMA4D binding molecule to be administered will be dependent upon the mode of administration and whether the subject will undergo a single dose or multiple doses of this agent.

This disclosure also provides for the use of an anti-SEMA4D binding molecule, e.g., an antibody or antigen-binding fragment, variant, or derivative thereof, in the manufacture of a medicament for treating an autoimmune disease and/or inflammatory disease, including, e g., arthritis, multiple sclerosis, CNS and PNS inflammatory diseases, neurodegenerative diseases, or cancer.

This disclosure also provides for the use of an anti-SEMA4D binding molecule, e.g., antibody of this disclosure, or antigen-binding fragment, variant, or derivative thereof, in the manufacture of a medicament for treating an autoimmune disease and/or inflammatory disease, including, e.g., arthritis, multiple sclerosis, CNS and PNS inflammatory diseases, neurodegenerative diseases, or cancer, wherein the medicament is used in a subject that has been pretreated with at least one other therapy. By "pretreated" or "pretreatment" is intended the subject has received one or more other therapies (e.g., been treated with at least one other cancer therapy) prior to receiving the medicament comprising the anti-SEMA4D binding molecule. "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising an anti-SEMA4D binding molecule, e.g., an antibody or antigen-binding fragment, variant, or derivative thereof as provided herein. It is not necessary that the subject was a responder to pretreatment with the prior therapy or therapies. Thus, the subject that receives the medicament comprising the anti-SEMA4D binding molecule could have responded, or could have failed to respond (e.g., the cancer was refractory), to pretreatment with the prior therapy, or to one or more of the prior therapies where pretreatment comprised multiple therapies. Examples of other cancer therapies for which a subject can have received pretreatment prior to receiving the medicament comprising an anti-SEMA4D binding molecule, e.g., an antibody or antigen-binding fragment, variant, or derivative thereof as provided herein include, but are not limited to, surgery; radiation therapy; chemotherapy, optionally in combination with autologous bone marrow transplant; other anti-cancer monoclonal antibody therapy; small molecule-based cancer therapy;
vaccine/immunotherapy-based cancer therapies; steroid therapy; other cancer therapy; or any combination thereof.

IX. Diagnostics

This disclosure further provides a diagnostic method useful during diagnosis of SEMA4D-mediated diseases such as certain types of cancers, autoimmune diseases, inflammatory diseases including, e.g., arthritis, multiple sclerosis, central nervous system (CNS) and peripheral nervous system (PNS) inflammatory diseases, neurodegenerative diseases, and invasive angiogenesis, which involves measuring the expression level of SEMA4D protein or transcript in tissue or other cells or body fluid from an individual and comparing the measured expression level with a standard SEMA4D expression level in normal tissue or body fluid, whereby an increase in the expression level compared to the standard is indicative of a disorder.

An anti-SEMA4D binding molecule, e.g., an antibody or antigen-binding fragment, variant, or derivative thereof as provided herein can be used to assay SEMA4D protein levels in a biological sample using classical immunohistological methods known to those of skill in the art (e.g., see Jalkanen, et al., J. Cell. Biol. 101:976-985 (1985); Jalkanen et al., J. Cell Biol. 105:3087-3096 (1987)). Other antibody-based methods useful for detecting SEMA4D protein expression include immunoassays, such as the enzyme linked immunosorbent assay (ELISA), immunoprecipitation, or Western blotting. Suitable assays are described in more detail elsewhere herein.

By "assaying the expression level of SEMA4D polypeptide" is intended qualitatively or quantitatively measuring or estimating the level of SEMA4D polypeptide in a first biological sample either directly (e.g., by determining or estimating absolute protein level) or relatively (e.g., by comparing to the disease associated polypeptide level in a second biological sample). In certain aspects, SEMA4D polypeptide expression level in the first biological sample can be measured or estimated and compared to a standard SEMA4D polypeptide level, the standard being taken from a second biological sample obtained from an individual not having the disorder or being determined by averaging levels from a population of individuals not having the disorder. As will be appreciated in the art, once the "standard" SEMA4D polypeptide level is known, it can be used repeatedly as a standard for comparison.

By "biological sample" is intended any biological sample obtained from an individual, cell line, tissue culture, or other source of cells potentially expressing SEMA4D. Methods for obtaining tissue biopsies and body fluids from mammals are well known in the art.

X. Immunoassays

An anti-SEMA4D binding molecule, e.g., an antibody or antigen-binding fragment, variant, or derivative thereof as provided herein can be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety). Exemplary immunoassays are described briefly below (but are not intended by way of limitation).

An anti-SEMA4D binding molecule, e.g., an antibody or antigen-binding fragment, variant, or derivative thereof as provided herein, additionally, can be employed histologically, as in immunofluorescence, immunoelectron microscopy or non-immunological assays, for in situ detection of SEMA4D protein or conserved variants or peptide fragments thereof. In situ detection can be accomplished by removing a histological specimen from a patient, and applying thereto a labeled anti-SEMA4D antibody, or antigen-binding fragment thereof, e.g., by overlaying the labeled antibody (or fragment) onto a biological sample. Through the use of such a procedure, it is possible to determine not only the presence of SEMA4D protein, or conserved variants or peptide fragments, but also its distribution in the examined tissue. Using this disclosure, those of ordinary skill will readily perceive that any of a wide variety of histological methods (such as staining procedures) can be modified in order to achieve such in situ detection.

The binding activity of a given lot of an anti-SEMA4D binding molecule, e.g., an antibody or antigen-binding fragment, variant, or derivative thereof as provided herein can be determined according to well-known methods. Those skilled in the art will be able to determine operative and optimal assay conditions for each determination by employing routine experimentation.

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities.

Surface plasmon resonance (SPR) as performed on BIACORE® offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIApplications Handbook, version AB (reprinted 1998), BIACORE® code No. BR-1001-86; BIAtechnology Handbook, version AB (reprinted 1998), BIACORE® code No. BR-1001-84. SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIACORE® measurements monitor interactions directly as they happen. The technique is well suited to determination of kinetic parameters. Comparative affinity ranking is simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIACORE® investigations. The range of affinities measurable by this technique is very broad ranging from mM to pM.

Epitope specificity is an important characteristic of a monoclonal antibody. Epitope mapping with BIACORE®, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIACORE® are straightforward to carry out.

For example, one can use a capture molecule to bind the first Mab, followed by addition of antigen and second MAb sequentially. The sensorgrams will reveal: (1) how much of the antigen binds to first Mab, (2) to what extent the second MAb binds to the surface-attached antigen, (3) if the second MAb does not bind, whether reversing the order of the pair-wise test alters the results.

Peptide inhibition is another technique used for epitope mapping. This method can complement pair-wise antibody binding studies and can relate functional epitopes to structural features when the primary sequence of the antigen is known. Peptides or antigen fragments are tested for inhibition of binding of different MAbs to immobilized antigen.

Peptides which interfere with binding of a given MAb are assumed to be structurally related to the epitope defined by that MAb.

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described can be followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein J., Immunology: The Science of Self-Nonself Discrimination (John Wiley & Sons, NY (1982)); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; W.H. Freeman and Co., NY); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall, 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

Example 1: Generation of Fully Human Anti-SEMA4D Monoclonal Antibody MAb D2517

Fully human anti-SEMA4D monoclonal antibody D2517 was generated by the following method. Libraries of fully human antibodies generated in vaccinia virus and were screened for binding to SEMA4D according methods described in US Patent Appl. Publication No. 2013-0288927-A1, which is incorporated herein by reference in its entirety. A total of 96 antibodies were binned into six different epitope groups by competition ELISA. Competitive binding of human antibodies to the native form of human SEMA4D on Jurkat cells was assessed using mouse antibodies, mAb76 and mAb67, and a mouse IgG control. mAb76 and mAb67 bind to known epitopes of human SEMA4D, and competition with either indicates functionality. Jurkat cells were pre-incubated for 30 minutes on ice with mAb76, mAb67 or mouse IgG control at 5 ug/mL in 100 uL and 200,000 cells in FACS buffer (1XPBS+0.05% BSA+2 mM EDTA). This allowed saturating binding of the mouse antibodies blocking the binding epitopes. The human test antibodies and control antibodies were preincubated at 1 ug/mL on ice for 30 minutes with a secondary reagent goat anti-human Fc-Dylight 649 antibody (Jackson Immunoresearch 496-170). Following incubation of Jurkat cells with mouse IgG antibodies, the cells were washed and incubated with the test antibody/secondary complex mixture for 30 minutes on ice. The cells were subsequently washed two times with 200 uL of FACS buffer and resuspended in a fixing solution of 250 μL of PBS/1% BSA and 0.5% paraformaldehyde with PI. Following resuspension, the cells were analyzed by flow cytometry on a FACS CANTO II. The PI negative population was gated and Dylight649 shift was recorded and assessed. Percent inhibition of binding has been calculated in comparison to binding of the human antibodies to Jurkat cells preincubated with irrelevant mouse IgG.

MAb C2305 was selected for further characterization due to its ability to cross-block of previously-characterized murine anti-SEMA4D antibodies 67-2 and 76-1. See, e.g., U.S. Pat. No. 8,496,938, the disclosure of which is incorporated herein by reference in its entirety.

A polynucleotide encoding the MAb C2305 VH was cloned into a mammalian expression vector that contained the human gamma-4 heavy chain constant region coding sequence, creating a full length heavy chain. A polynucleotide encoding the MAb C2305 VL was cloned into a mammalian expression vector that had the human lambda constant region coding sequence, creating a full length light chain. The expression vectors containing the heavy chain and the light chain were co-transfected into CHO-S cells. The monoclonal antibody that was produced was secreted from the cells and harvested after a 3-6-day expression period. The resulting MAb was purified using Protein A chromatography and characterized. The resulting fully human MAb (MAb C2305) was demonstrated to be specific for SEMA4D by flow cytometry and by ELISA, and was shown to be able to compete with murine MAb 67-2 for binding to SEMA4D. The functional activity of MAb C2305 was further evaluated in a Receptor Blocking Assay according to the method in Example 3, below. Receptor blocking was observed but at a lower level than that of the humanized MAb 2503 (U.S. Pat. No. 8,496,938, also referred to as VX15/2503) which was used as a comparator.

MAb C2305 was fully sequenced and was then engineered for affinity improvement.

The heavy chain complementarity determining region 3 (HCDR3) was subjected to standard site-directed mutagenesis techniques, and a new fully human light chain variable region (VL) was identified using from a light chain library according to methods described in US Patent Appl. Publication No. 2013-0288927-A1. From these alterations a MAb with improved affinity, MAb D2517, was selected as the lead antibody. MAb D2517 was cloned, assembled, and expressed as a fully human IgG4 antibody with a lambda light chain. The VH, VL, and CDR sequences of MAb D2517 are presented in Table 2.

TABLE 2

MAb D2517 Sequences

| SEQ ID NO | STRUCTURE | SEQUENCE |
|---|---|---|
| 1 | VH | EVQLVESGGGLVQPGGSLRLSCAASGFIFSDYW MVWVRQAPGKGLEYVAHMNQDGGARYYAESVRG RFTISRDNAKNSLYLQMNSLRAEDTAVYYCARD PWGYDSWGQGTLVT |
| 2 | HCD1 | DYWMV |
| 3 | HCDR2 | HMNQDGGARYY |
| 4 | HCDR3 | DPWGY |
| 5 | VL | SYELTQPPSVSVSPGQTASITCSGDKLGDKYAV WYQQKPGQSPVLVIYQDSKRPSGIPERFSGSNS GNTATLTISGTQAMDEADYYCQAWEQEAAWVFG GGTKL |
| 6 | LCDR1 | SGDKLGDKYAV |
| 7 | LCDR2 | QDSKRPS |
| 8 | LCDR3 | QAWEQEAAWV |

Example 2: Binding Characterization of MAb D2517

The binding characteristics of MAb D2517 were determined by BIACORE assay, as follows. The antibody, as well as the comparator antibody VX15/2503, both formulated in PBS, were captured onto the sensor with goat anti-human IgGFc at low density and then marmoset SEMA4D-His was flowed over the captured antibody at an antigen concentration range of 0-25 nm. The results are shown in Table 3. The affinity of MAb D2517 for SEMA4D was similar to the affinity of VX15/2503.

TABLE 3

BIACORE Assay Results

| | Marmoset SEMA4D | | | |
|---|---|---|---|---|
| MAb | ka (1/MS) | kd (1/S) | KA (1/M) | KD (nM) |
| MabD2517 | 7.89E+05 | 3.20E−03 | 2.47E+08 | 4.00 |
| VX15/2503 | 2.43E+05 | 1.18E−03 | 2.06E+08 | 4.86 |
| VX15/2503 | 3.02E+05 | 1.26E−03 | 2.40E+08 | 4.17 |

The ability of MAb D2517 to bind to human, mouse, marmoset, and cynomolgus monkey SEMA4D was determined by ELISA using the following method. Nunc maxisorp C-well ELISA plates were coated overnight with 100 µL/well of CD100-His formulated in 1× PBS. Following the overnight incubation, plates were washed and subsequently blocked with 200 µL/well with PBS+0.5% BSA+0.025% tween 20 for least 1 hour at room temperature. After additional washing, 100 µl/well diluted MAbs (100 ng/mL) were added to each well of the ELISA plate, which was incubated at room temperature for 2 hours and then washed. Next, 100 µl/well of 1:10,000 goat anti-human Fc (Jackson cat #109-035-098 lot 118460) was added to each well, and the ELISA plate was incubated at room temperature for 1 hour. The plate was then washed and developed with 100 uL/well TMB substrate for 15 minutes. The detection reaction was stopped using 100 uL/well 2N sulfuric acid, and the plate was read using a Plate Reader at a wavelength of 450-570 nM.

The results are shown in FIG. 1A (human SEMA4D), FIG. 1B (marmoset SEMA4D), FIG. 1C (cyno SEMA4D), and FIG. 1D (mouse SEMA4D).

Example 3: MAb D2517 Blocks SEMA4D from Binding to its Receptor

The ability of MAbD2517 to block SEMA4D derived from various species to bind to its receptor, Plexin B 1, was tested as follows.

MAbD2517 and MAbVX15/2503 were formulated in acetate buffer. The antibodies were compared in triplicate dilution series for their ability to block SEMA4D-His complexes (human, cynomolgus monkey, mouse, or rat SEMA4D) from binding to 293PLXNB1 cells. All antibodies diluted from 1.5 µg/mL to 88 ng/mL in a 96 well plate and combined 1:1 with 0.8 ug/mL of the appropriate SEMA4D-His and incubated overnight at 4° C.

The next day the Antibody/SEMA4D-His complexes or controls were added to $2.5 \times 10^5$ 293 PLXNB1 cells in a 96 well plate and binding was allowed to occur for 30 min at 4° C. After washing, the cells were stained with anti-6xHis-APC (30 min, 4° C.), washed and analyzed by flow cytometry on FACS Canto II. The results are shown in FIG. 2A-2D. EC50 values were calculated from the curves and are shown in TABLE 4.

TABLE 4

| EC50 Values (in nM) for Blocking SEMA4D from Binding to its Receptor | | |
|---|---|---|
| SEMA4D-his | VX15/2503 | MAb D2517 |
| Human SEMA4D | 0.3 | 1.0 |
| Cyno SEMA4D | 0.5 | 1.2 |
| mouse SEMA4D | 0.4 | 1.2 |
| rat SEMA4D | 0.6 | 1.5 |

Example 4: Testing of Murine Chimeric Equivalent of MAbD2517 in a Tumor Model

The VH and VL amino acid sequences (SEQ ID NO: 1 and SEQ ID NO: 5) of MAb D2517 were inserted into vectors expressing the murine IgG1 and lambda constant regions to produce the chimeric antibody MAb D2585. The antibody was expressed in CHO-S cells and purified as explained in Example 1.

Balb/c female mice of 6-8 weeks of age (n=12) were grafted with 30,000 Tubo.A5 breast tumor cells subcutaneously into the mammary fat pads of the mice. Treatment with control Mouse IgG1/2B8.1E7 or anti-SEMA4D chimeric antibody MAbD2585 was initiated 7 days post inoculation (10 mg/kg, IP, weekly X5). Tumors were measured with calipers 2×/week starting 11 days post implant. Animals were sacrificed when tumor volume reached 800 mm$^3$.

Figure 3A:
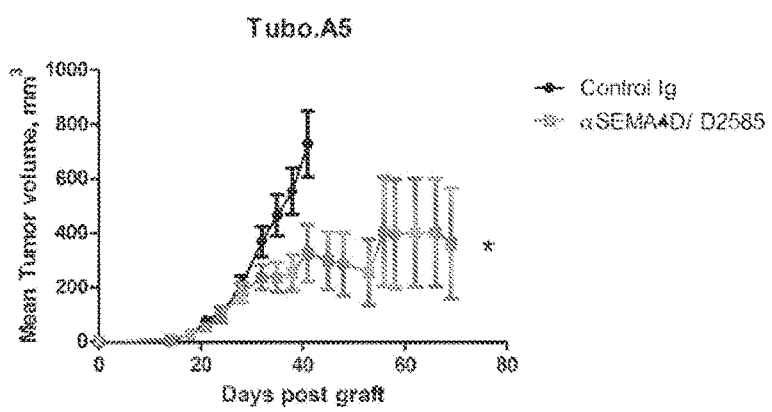
FIG. 3A shows measurement of tumor volume in Balb/c mice treated with either control Mouse IgG1/2B8 or a chimeric antibody MAbD2585 (10 mg/kg, IP, weekly X5).
Figure 3B:
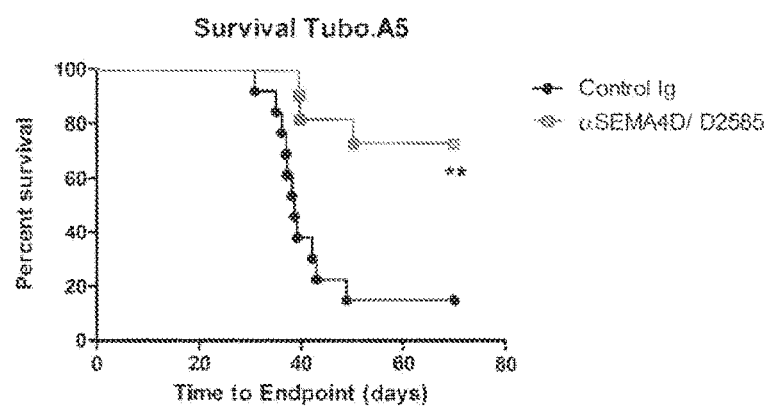
FIG. 3B shows survival time of Balb/c mice treated with either control Mouse IgG1/2B8 or chimeric antibody MAbD2585.

Tumor growth was measured by calipers and measurements were used to calculate tumor volume using the formula (w$^2$×1/2, where w=width, smaller measurement, and l=length, in mm, of the tumor. Mean tumor volume and Kaplan Meier survival curves, defined as time to endpoint where tumor volume=800 mm$^3$, are shown in FIGS. 3A and 3B, respectively. Statistical analyses were conducted using Two-way Analysis of Variance (ANOVA) for mean tumor volume ($p<0.05$), and Log Rank analysis for survival ($p<0.0.1$), respectively, which were statistically significant.

The frequency of tumor regressions in Tubo tumor model was also measured and is shown in FIG. 3C. Regression is the lack of palpable tumor, defined as a tumor measuring <50 mm$^3$ for at least two consecutive measurements. Treatment with chimeric antibody MAbD2585 increased the number of regressions in Tubo-bearing mice. The number of regressions in the chimeric antibody MAbD2585-treated mouse group was statistically significant compared to Control Ig ($p=0.01$), as determined by Fisher's Exact test.

The breadth and scope of the present disclosure should not be limited by any of the above-described exemplary embodiments but should be defined only in accordance with the following claims and their equivalents.

The invention claimed is:

1. A composition comprising an antibody or antigen-binding fragment thereof that specifically binds to semaphorin-4D (SEMA4D) comprising a heavy chain variable region (VH) and a light chain variable region (VL), wherein the VH comprises complementarity determining regions (HCDRs) HCDR1, HCDR2, and HCDR3 comprising amino acid sequences SEQ ID NO: 2, SEQ ID NO: 3, and SEQ ID NO: 4, respectively; and wherein the VL comprises complementarity determining regions (LCDRs) LCDR1, LCDR2, and LCDR3 comprising amino acid sequences SEQ ID NO: 6, SEQ ID NO: 7, and SEQ ID NO: 8, respectively; and
   wherein the VH comprises an amino acid sequence at least 80%, 85%, 90%, 95%, or 100% identical to SEQ ID NO: 1 and/or the VL comprises an amino acid sequence at least 80%, 85%, 90%, 95%, or 100% identical to SEQ ID NO: 5.

2. The composition of claim 1, wherein the VH further comprises framework regions (HFWs) HFW1, HFW2, HFW3, and HFW4, and wherein the VL further comprises framework regions (LFWs) LFW1, LFW2, LFW3, and LFW4.

3. The composition of claim 2, wherein the framework regions are human antibody framework sequences.

4. The composition of claim 2, wherein the framework regions are non-human antibody framework sequences.

5. The composition of claim 1, further comprising a heavy chain constant region or fragment thereof fused to the C-terminus of the VH.

6. The composition of claim 5, wherein the heavy chain constant region or fragment thereof is a human heavy chain constant region.

7. The composition of claim 6, wherein the heavy chain constant region or fragment thereof is a human IgG4 constant region.

8. The composition of claim 5, wherein the heavy chain constant region or fragment thereof is a non-human heavy chain constant region.

9. The composition of claim 8, wherein the heavy chain constant region or fragment thereof is a murine IgG1 constant region.

10. The composition of claim 1, further comprising a light chain constant region or fragment thereof fused to the C-terminus of the VL.

11. The composition of claim 10, wherein the light chain constant region or fragment thereof is a human light chain constant region.

12. The composition of claim 11, wherein the light chain constant region or fragment thereof is a human lambda light chain constant region.

13. The composition of claim 10, wherein the light chain constant region or fragment thereof is a non-human light chain constant region.

14. The composition of claim 13, wherein the light chain constant region or fragment thereof is a murine lambda light chain constant region.

15. The composition of claim 1, which is an Fab fragment, an Fab' fragment, an F(ab')2 fragment, an Fd fragment, a single-chain Fv fragment (scFv), or a disulfide-linked Fv fragment (sdFv).

16. The composition of claim 1, which is multispecific.

17. A method for neutralizing SEMA4D in a human subject, comprising administering to the human subject the composition of claim 1.

18. A method of treating cancer in a subject, comprising administering to the subject the composition of claim 1.

19. The method of claim 18, wherein the cancer is a solid tumor that expresses Semaphorin 4D (SEMA4D) or a SEMA4D receptor.

20. The method of claim 18, wherein the method further comprises administering another anti-cancer antibody therapy, a small molecule-based cancer therapy, or a vaccine/immunotherapy-based cancer therapy to the subject.

21. The method of claim 20, wherein the composition and the anti-cancer antibody therapy, the small molecule-based cancer therapy or the vaccine/immunotherapy-based cancer therapy are co-administered or administered separately.

22. The composition of claim 1, further comprising an immunosuppressive or anti-inflammatory agent.

23. The method of claim 17, wherein the subject has an autoimmune disease or disorder, an inflammatory disease or disorder, cancer, a neuroinflammatory disease or disorder, a neurodegenerative disease or disorder, or any combination thereof.

24. The method of claim 23, wherein the method further comprises administering an immunosuppressive agent or anti-inflammatory agent.

25. The method of claim 23, wherein the method further comprises administering an anti-cancer antibody therapy, a small molecule-based cancer therapy or a vaccine/immunotherapy-based cancer therapy.

26. The method of claim 23, wherein the autoimmune disease is an osteodegenerative disease.

27. The composition of claim 1, wherein the antibody or antigen-binding fragment thereof inhibits binding of SEMA4D to its receptor.

* * * * *